United States Patent [19]

Gaur et al.

[11] Patent Number: 5,948,764
[45] Date of Patent: Sep. 7, 1999

[54] METHODS FOR TREATMENT OF MULTIPLE SCLEROSIS UTILIZING PEPTIDE ANALOGUES OF HUMAN MYELIN BASIC PROTEIN

[75] Inventors: Amitabh Gaur, San Diego; Paul J. Conlon, Solana Beach; Nicholas Ling, San Diego, all of Calif.

[73] Assignee: Neurocrine Biosciences, Inc., San Diego, Calif.

[21] Appl. No.: 08/781,122

[22] Filed: Jan. 9, 1997

Related U.S. Application Data

[63] Continuation-in-part of application No. 08/402,992, Mar. 9, 1995, abandoned.

[51] Int. Cl.$^6$ .................................................. A61K 38/00
[52] U.S. Cl. ............................... 514/14; 514/12; 514/13; 514/15; 514/16; 514/903; 530/324; 530/325; 530/326; 530/327; 530/328; 530/329
[58] Field of Search ..................................... 530/324, 325, 530/326, 327, 328, 329; 514/12–16, 903

[56] References Cited

FOREIGN PATENT DOCUMENTS

| | | |
|---|---|---|
| WO 92/21367 | 12/1992 | WIPO . |
| WO 93/08212 | 4/1993 | WIPO . |
| WO 93/21222 | 10/1993 | WIPO . |
| WO 95/08572 | 3/1995 | WIPO . |
| WO 96/16085 | 5/1996 | WIPO . |
| WO 96/16086 | 5/1996 | WIPO . |

OTHER PUBLICATIONS

HCAPLUS AN 1994:45950, Weiner et al., WO 9321222, (abstract) Oct. 28, 1993.
Rudinger S., *Peptide Hormones*, pp. 1–6, Jun. 1976.
Abstract 65027 from *Biol. Abstr.* 81(7):AB–701 (1985) of the article "Monoclonal antibodies to human myelin basic protein," by Chou et al., *J. Neurochem.* 46(1):47–53, 1985.
Acha–Orbea et al., "Limited Heterogeneity of T Cell Receptors from Lymphocytes Mediating Autoimmune Encephlomyelitis Allows Specific Immune Intervention," *Cell* 54:263–273, 1988.
Babbitt et al., "Antigenic competition at the level of peptide–Ia binding," *Proc. Natl. Acad. Aci. USA* 83:4509–4513, 1986.
Bernard C., "Experimental Autoimmune Encephalomyelitis in Mice: Genetic Control of Susceptibility," *Journal of Immunogenetics* 3:263–274, 1976.
Brocke et al., "In Vitro Proliferative Responses and Antibody Titers Specific to Human Acetylcholine Receptor Synthetic Peptides in Patients with *Myasthemia gravis* and Relation to HLA Class II Genes," *J. Clin. Invest.* 82:1894–1900, 1988.
Brostoff and Howell, "T Cell Receptors, Immunoregulation and Autoimmunity," *Clinical Immunology and Immunopathology*, 62(1):1–7, 1992.
Carter and Rodriguez, "Immunosuppressive Treatment of Multiple Sclerosis," *Mayo Clin. Proc.* 64:664–669, 1989.

Chou et al., "Identity of Myelin Basic Protein from Multiple Sclerosis and Human Control Brains: Discovery of a Genetic Variant," *Jounral of Neurochemistry*, 30:745–750, 1978.
Day et al., "The Polyclonal Antibody Responses of Lewis Rats to the Synthetic Encephaloitogenic Neuropeptide S55S (Residues 72–84 of Guinea Pig Myelin Basic Protein) and Its Analogs," *Journal of Neuroscience Research* 18:214–221, 1987.
Einstein et al., "Suppression of Experimental Allergic Encephalomyelitis By Chemically Modified Encephalitogen," *Ummunochemistry* 9:1013–1019, 1972.
Evavold and Allen, "Separation of IL–4 Production from the Th Cell Proliferation by an Altered T Cell Receptor Ligand," *Science* 225:1308–1310, 1991.
Gammon et al., "Neonatal T–cell tolerance to minimal immunogenic peptides is caused by clonal inactivation," *Nature*, 319:413–415, 1986.
Gaur et al., "Amelioration of Autoimmune Encephlomyelitis By a Nonimmunogenic Non–Self Peptide That Binds to I–A$^U$," *Journal of Immunology* 148(10):3049–3054, 1992.
Gautam et al., "A Polyalanine Peptide with only Five Native Myelin Basic Protein Residues Induces Autoimmune Encephalomyelitis," *J. Exp. Med.* 176:605–609, 1992.
Gautam et al., "Inhibition of Experimental Autoimmune encephalomyelitis by Myelin Basic Protein Synthetic peptide–Induced Anergy," *Science* 258L 1491–1494, 1992.
Hadaen et al., "Thymic Hormones, Interleukins, Endotoxin and Thymomimetic Drugs in T Lymphocyte Ontogeny," in *Advance in Immunopharmacology 3*, L. Chedid et al. (Eds.), 1985, pp. 487–497.
Hashim and Day, "Synthetic Peptide Analogs to Probe the Immunological Expression of the Rat Encephalitogenic Neuropeptide," *Journal of Neuroscience Research* 18:209–213, 1987.
Hashim et al., "Suppression and Reversal of Allergic Encephalomyelitis in Guinea Pigs with a Non–Encephalotigenic Analogue of the Trytophan Region of the Myelin Basic Protein," *Journal of Immunology* 116(1): 126–130, 1976.
Hashim, G., "Experimental Allergic Encephalomyelitis: Activation of Suppressor T Lymphocytes By a Modified Sequence of the T Effector Determinant," *Journal of Immunology* 126(2):419–423, 1981.

(List continued on next page.)

*Primary Examiner*—Cecilia J. Tsang
*Assistant Examiner*—C. Delacroix-Muirheid
*Attorney, Agent, or Firm*—Seed and Berry LLP

[57] ABSTRACT

The present invention is directed toward peptide analogues of human myelin basic protein for use in the treatment of multiple sclerosis. Within one aspect, peptide analogues suitable for treating multiple sclerosis are provided which are at least seven amino acids long and derived from residues 86 to 99 of human myelin basic protein. In addition, such analogues may be altered from the native sequence at positions 87, 88, 97, 98 or 99 to a D-amino acid. Additional alterations may be made at other positions. Pharmaceutical compositions containing these peptide analogues are also provided, as well as methods for treating multiple sclerosis.

6 Claims, 22 Drawing Sheets

OTHER PUBLICATIONS

Jahnke et al., "Sequence Homology Between Certain Viral Proteins and Proteins Related to Encephalomyelitis and Neuritis," *Science* 229:282–284, 1985.

Kardys and Hashim, "Experimental Allergic Encephalomyelitis in Lewis Rats: Immunoregulation of Disease–Inducing Determinant," *Journal of Immunology* 127(3):862–866, 1981.

Karin et al., "Reversal of Experimental Autoimmune Encephalomyelitis by a Soluble Peptide Variant of a Myelin Basic Protein Epitope: T Cell Receptor Antogonism and Reduction of Interferon γ and Tumor Necrosis Factor β Production," *J. Exp. Med.* 180: 2227–2237, 1984.

Kira et al., "Experimental Allergic Encephalomyelitis in Rabbits. A Major Encephalitogenic Determinant within Residues 1–44 of Myelin Basic Protein," *J. of Neuroimmunol.* 12(3):183–193, 1986.

Kuchroo et al., "A Single TCR Antagonist Peptide Inhibits Experimental Allergic Encephalomyelitis Mediated by a Diverse T Cell Repertoire," *Journal of Immunology* 153: 3326–3336, 1994.

Lamont et al., "Inhibition of Experimental Autoimmune Encephalomyelitis Induction In SJL/J Mice By Using A Peptide With High Affinity For IA$^s$ Molecules," *Journal of Immunology* 145(6):1687–1693, 1990.

Lehinger, A., "The Amino Acid Building Blocks of Proteins," in *Biochemistry, 2$^{nd}$* ed., Worth Publishers, Inc. pp. 71–75, 1975.

Martin et al., "A Myelin Basic Protein Peptide Is Recognized by Cytotoixc T Cells in the Context of Four HLA–DR Types Associated with Multiple Sclerosis," *Journal of Experimental Medicine* 173:19–24, 1991.

Martin et al., "Diversity in Fine Specificity and T Cell Receptor Usage of the Human CD4$^+$Cytotoxic T Cell Response Specific for the Immunodominant Myelin Basic Protein Peptide 87–106," *Journal of Immunology* b148(5):1359–1366, 1992.

Martin et al., "Immunological Aspects of Demyelinating Disease," *Annu. Rev. Immunol.* 10:153–87, 1992.

Rothbard and Taylor, "A sequence pattern common to T cell eptiopes," *EMBO J.* 7(1):93–100, 1988.

Rothbard, J., "Peptides and Cellular Immune Response," *Ann. Inst. Pasteur/Virologie* 137 E:518–526, 1986.

Rudinger, J., "Characteristics of the amino acids as components of a peptide hormone sequence," in *Peptide Hormones,* J. A. Parsons (ed.), University Park Press, Baltimore, pp. 1–7, 1976.

Sakai et al., "Prevention of experimental encephalomyelitis with peptides that block interaction of T cells with major histocompatibility complex proteins," *Proc. Natl. Acad. Sci. USA* 86:9470–9474, 1989.

Servis et al., "Two adjacent epitopes on a synthetic dodecapeptide induce lactate dehydrogenase B–specific helper and suppressor T cells," *Proc. R. Soc. Lond. B* 228:461–470, 1986.

Sette et al., "Analysis of lysozyme–specific immune responses by synthetic peptides. I. Characterization of antibody and T cell–mediated repsonses to the N–terminal peptide of hen egg–white lysozyme," *Eur. J. Immunol.* 16:1–6, 1986.

Smilek et al., "A single amino acid change in a myelin basic protein peptide confers the capacity to prevent rather than induce experimental autoimmune encephlomyelitis," *Proc. Natl. Acad. Sci. USA* 88:9633–9637, 1991.

Sriram et al., "Administration of Myelin Basic Protein-–coupled Spleen Cells Prevents Experimental Allergic Encephalitis," *Cellular Immunology* 75:378–382, 1983.

Steinman et al., "Natural occurence of thymocytes that react with myelin basic protein," *Neurology* 30(7):755–759, 1980.

Steinman et al., "Regulation of autosensitisation to encephalitogenic myelin basic protein by macrophage–associated and soluble antigen," *Nature* 265:173–175, 1977.

Steinman et al., "The Epigenetics of Multiple Sclerosis: Clues to Etiology and A Rational for Immune Therapy," *Annu. Rev. Neuorsci.* 17:247–265, 1994.

Su et al., "Synthetic Myelin basic Protein Peptide Analogs Are Specific Inhibitors of Phospholipid/Calcium–Dependent Protein Kinase (Protein Kinase C)," *Biochemical and Biophysical Research Communications* 134(1):78–84, 1986.

Talmadge et al., "Screening Models for Biological Response Modifiers," in *13$^{th}$ International Congress of Chemotherapy. Symposium, Biological Response Modifiers; SY 64 part 203,* Vienna Aug. 28–Sep. 2, 1993, pp. 203/19–203/34.

Teitelbaum et al., "Specific inhibition of the T–cell response to myelin basic protein by the synthetic copolymer Cop 1," *Proc. Natl. Acad. Sci. USA* 85:9724–9728, 1988.

Vogt et al., "Ligands Motifs of HLA–DRB5*0101 and DRB1*1501 Molecules Delineated from Self–Peptides," *Journal of Immunology,* 153:1665–1673, 1994.

Wraith et al., "Antigen Recognition in Autoimmune Encephalomyelitis and the Potential for Peptide–Mediated Immunotherapy," *Cell* 59:247–255, 1989.

Wraith et al., "T Cell Recognition as the Target for Immune Intervention in Autoimmune Disease," *Cell* 57:709–715, 1989.

Wucherpfennig et al., "Structural Requirements for Binding of an Immunodominant Myellin Basic Protein Peptide to DR2 Isotypes and for Its Recognition by Human T Cell Clones," *J. Exp. Med.* 179:279–290, 1991.

Zamvil and Steinman, "The T Lymphocyte in Experimental Allergic Encephalomyelitis," *Annu. Rev. Immunol.* 8:579–621, 1990.

Zamvil et al., "Encephalitogenic T Cell Clones Specific for Myelin basic Protein," *J. Exp. Med.* 162:2107–2124, 1985.

Zamvil et al., "Multiple Discrete Encephalitogenic Epitopes of the Autoantigen Myelin Basic Protein Include a Determinant for I–E Class II–Restricted T Cells," *J. Exp. Med.* 168: 1181–1186, 1988.

Zamvil et al., "T–cell clones specific for myelin basic protein induce chronic relapsing paralysis and demyelination," *Nature,* 317:355–358, 1985.

Zamvil et al., "T–cell epitope of the autoantigen myelin basic protein that induces encephalomyelitis," *Nature* 324:258–260, 1986.

Zamvil et al., "T–Cell Specificity for Class II(I–A) and the Encephalotogenic N–Terminal Epitope of the Autoantigen Myelin Basic Protein," *Journal of Immunology* 139(4): 1075–1079, 1987.

```
ATGGCGTCACAGAAGAGACCCTCCCAGAGGCACGGATCCAAGTACCTGGCCACAGCAAGTACCATGGACC   70
         1
   M  A  S  Q  K  R  P  S  Q  R  H  G  S  K  Y  L  A  T  A  S  T  M  D    22
ATGCCAGGCATGGCTTCCTCCCAAGGCACAGAGACACGGGCATCCTTGACTCCATCGGGCGCTTCTTTGG   140

H  A  R  H  G  F  L  P  R  H  R  D  T  G  I  L  D  S  I  G  R  F  F  G   46
CGGTGACAGGGGTGCGCCAAAGCGGGGCTCTGGCAAGGACTCACACCACCCGGCAAGAACTGCTCACTAT   210

G  D  R  G  A  P  K  R  G  S  G  K  D  S  H  H  P  A  R  T  A  H  Y   69
GGCTCCCTGCCCCAGAAGTCACACGGCCGGACCCAAGATGAAAACCCCGTAGTCCACTTCTTCAAGAACA   280

G  S  L  P  Q  K  S  H  G  R  T  Q  D  E  N  P  V  V  H  F  F  K  N    92
TTGTGACGCCTCGCACACCACCCCCGTCGCAGGGAAAGGGGAGAGGACTGTCCCTGAGCAGATTTAGCTG   350

I  V  T  P  R  T  P  P  P  S  Q  G  K  G  R  G  L  S  L  S  R  F  S  W   116
GGGGGCCGAAGGCCAGAGACCAGGATTTGGCTACGGAGGCAGAGCGTCCGACTATAAATCGGCTCACAAG   420

G  A  E  G  Q  R  P  G  F  G  Y  G  G  R  A  S  D  Y  K  S  A  H  K   139
GGATTCAAGGGAGTCGATGCCCAGGGCACGCTTTCCAAAATTTTTAAGCTGGGAGGAAGAGATAGTCGCT   490

G  F  K  G  V  D  A  Q  G  T  L  S  K  I  F  K  L  G  G  R  D  S  R    162
CTGGATCACCCATGGCTAGACGCTGA   516

METHODS FOR TREATMENT OF MULTIPLE SCLEROSIS UTILIZING PEPTIDE ANALOGUES OF HUMAN MYELIN BASIC PROTEIN

CROSS-REFERENCE TO RELATED APPLICATIONS

This application is a continuation-in-part of U.S. patent application Ser. No. 08/402,992, filed Mar. 9, 1995, now abandoned.

TECHNICAL FIELD

The present invention relates generally to methods for treating multiple sclerosis utilizing peptide analogues of human proteins.

BACKGROUND OF THE INVENTION

Multiple sclerosis (MS) is a chronic, inflammatory disease that affects approximately 250,000 individuals in the United States. Although the clinical course may be quite variable, the most common form is manifested by relapsing neurological deficits, in particular, paralysis, sensory deficits, and visual problems.

The inflammatory process occurs primarily within the white matter of the central nervous system and is mediated by T lymphocytes, B lymphocytes, and macrophages. These cells are responsible for the demyelination of axons. The characteristic lesion in MS is called the plaque due to its macroscopic appearance.

Multiple sclerosis is thought to arise from pathogenic T cells that somehow evaded mechanisms establishing self-tolerance, and attack normal tissue. T cell reactivity to myelin basic protein may be a critical component in the development of MS. The pathogenic T cells found in lesions have restricted heterogeneity of antigen receptors (TCR). The T cells isolated from plaques show rearrangement of a restricted number of Vα and Vβ gene segments. In addition, the TCRs display several dominant amino acid motifs in the third complementarity determining region (CDR), which is the major antigen contact site. All together, three CDR3 motifs have been identified in T cell clones known to recognize an epitope within amino acids 86–106 of myelin basic protein. These motifs were found in 44% of rearranged TCR sequences involving one particular Vβ gene rearranged in T cells isolated from the brains of two patients with MS.

A definitive treatment for MS has not been established. Historically, corticosteroids and ACTH have been used to treat MS. Basically, these drugs reduce the inflammatory response by toxicity to lymphocytes. Recovery may be hastened from acute exacerbations, but these drugs do not prevent future attacks or prevent development of additional disabilities or chronic progression of MS (Carter and Rodriguez, *Mayo Clinic Proc.* 64:664, 1989; Weiner and Hafler, *Ann. Neurol.* 23:211, 1988). In addition, the substantial side effects of steroid treatments make these drugs undesirable for long-term use.

Other toxic compounds, such as azathioprine, a purine antagonist, cyclophosphamide, and cyclosporine have been used to treat symptoms of MS. Like corticosteroid treatment, these drugs are beneficial at most for a short term and are highly toxic. Side effects include increased malignancies, leukopenias, toxic hepatitis, gastrointestinal problems, hypertension, and nephrotoxicity (Mitchell, *Cont. Clin. Neurol.* 77:231, 1993; Weiner and Hafler, supra). Antibody based therapies directed toward T cells, such as anti-CD4 antibodies, are currently under study for treatment of MS. However, these agents may cause deleterious side effects by immunocompromising the patient.

More recently, cytokines such as IFN-γ and IFN-β have been administered in attempts to alleviate the symptoms of MS. However, a pilot study involving IFN-γ was terminated because 7 of 18 patients treated with this drug experienced a clinical exacerbation within one month after initiation of treatment. Moreover, there was an increase in the specific response to MBP (Weiner and Hafler, supra).

Betaseron, a modified beta interferon, has recently been approved for use in MS patients. Although Betaseron treatment showed some improvement in exacerbation rates (Paty et al., *Neurology* 43:662, 1993), there was no difference in the rate of clinical deterioration between treated and control groups (IFNB MS Study Group, *Neurology* 43:655, 1993; Paty et al., supra). Side effects were commonly observed. The most frequent of such side effects were fever (40%–58% of patients), flu-like symptoms (76% of patients), chills (46% of patients), myalgias (41% of patients), and sweating (23% of patients). In addition, injection site reactions (85%), including inflammation, pain, hypersensitivity and necrosis, were common (IFNB MS Study Group, supra; Connelly, *Annals of Pharm.* 28:610, 1994).

In view of the problems associated with existing treatments of MS, there is a compelling need for improved treatments which are more effective and are not associated with such disadvantages. The present invention exploits the use of peptide analogues of human myelin basic protein to effectively treat MS, while providing other related advantages.

SUMMARY OF THE INVENTION

As noted above, the present invention provides peptide analogues of human myelin basic protein which are suitable for treating multiple sclerosis. Within one aspect of the present invention, peptide analogues are provided comprising at least seven amino acids selected from residues 86 to 99 of human myelin basic protein, including residue 87, wherein L-valine at position 87 is altered to another amino acid, the peptide analogue having increased MHC binding relative to MBP 87–99. Within certain embodiments, L-valine at position 87 is altered to a D-amino acid such as D-valine, or to a D-amino acid selected from the group consisting of D-alanine, D-arginine, D-asparagine, D-aspartic acid, D-cysteine, D-glutamine, D-glutamic acid, D-glycine, D-histidine, D-isoleucine, D-leucine, D-lysine, D-methionine, D-phenylalanine, D-proline, D-serine, D-threonine, D-tryptophan and D-tyrosine. Within other embodiments, the N-terminal amino acid and/or C-terminal amino acids of the peptide analogue are altered to an amino acid, such that upon administration of the peptide analogue in vivo proteolysis or degradation is reduced.

Within other embodiments of the invention, the above-noted peptide analogues further include residue 98, wherein L-threonine at position 98 is altered to another amino acid, such as, for example, D-alanine, D-arginine, D-asparagine, D-aspartic acid, D-cysteine, D-glutamine, D-glutamic acid, D-glycine, D-histidine, D-isoleucine, D-leucine, D-lysine, D-methionine, D-phenylalanine, D-proline, D-serine, D-threonine, D-tryptophan, D-tyrosine and D-valine. Within yet further embodiments, any of the above-mentioned peptide analogues may also include residue 99, wherein L-proline at position 99 is altered to another amino acid. Representative examples of suitable D-amino acids include D-alanine, D-arginine, D-asparagine, D-aspartic acid, D-cysteine, D-glutamine, D-glutamic acid, D-glycine, D-histidine, D-isoleucine, D-leucine, D-lysine, D-methionine, D-phenylalanine, D-proline, D-serine, D-threonine, D-tryptophan, D-tyrosine and D-valine.

Within other aspects of the present invention, peptide analogues are provided comprising at least seven amino acids selected from residues 86 to 99 of human myelin basic protein, including residue 88, wherein L-histidine at position 88 is altered to another amino acid, the peptide analogue having increased MHC binding relative to MBP 87–99. Within one embodiment, L-histidine at position 88 is altered to a D-amnino acid such as D-alanine, or to another D-amino acid selected from the group consisting of D-arginine, D-asparagine, D-aspartic acid, D-cysteine, D-glutamine, D-glutamic acid, D-glycine, D-histidine, D-isoleucine, D-leucine, D-lysine, D-methionine, D-phenylalanine, D-proline, D-serine, D-threonine, D-tryptophan, D-tyrosine and D-valine. Within other embodiments, the N-terminal amino acid and/or C-terminal amino acids of the peptide analogue are altered to a D-amino acid, such that upon administration of the peptide analogue in vivo proteolysis is reduced. Within yet other embodiments, the peptide analogues described above may further include residue 98, wherein L-threonine at position 98 is altered to another amino acid, such as D-alanine, D-arginine, D-asparagine, D-aspartic acid, D-cysteine, D-glutamine, D-glutamic acid, D-glycine, D-histidine, D-isoleucine, D-leucine, D-lysine, D-methionine, D-phenylalanine, D-proline, D-serine, D-threonine, D-tryptophan, D-tyrosine or D-valine. Within another embodiment, peptide analogues are provided which include residue 99, wherein L-proline at position 99 is altered to another amino acid, such as, for example, D-alanine, D-arginine, D-asparagine, D-aspartic acid, D-cysteine, D-glutamine, D-glutamic acid, D-glycine, D-histidine, D-isoleucine, D-leucine, D-lysine, D-methionine, D-phenylalanine, D-proline, D-serine, D-threonine, D-tryptophan, D-tyrosine and D-valine.

Within yet another aspect of the present invention, peptide analogues are provided comprising at least seven amino acids selected from residues 86 to 99 of human myelin basic protein, including residue 98, wherein L-threonine at position 98 is altered to another amino acid, the peptide analogue having increased MHC binding relative to MBP 87–99. Within one embodiment, L-threonine at position 98 is altered to a D-amino acid such as D-alanine, D-arginine, D-asparagine, D-aspartic acid, D-cysteine, D-glutamine, D-glutamic acid, D-glycine, D-histidine, D-isoleucine, D-leucine, D-lysine, D-methionine, D-phenylalanine, D-proline, D-serine, D-threonine, D-tryptophan, D-tyrosine or D-valine. Within another embodiment, the N-terminal amino acid and/or C-terminal amino acids of the peptide analogue are altered to an amino acid, such that upon administration of the peptide analogue in vivo proteolysis is reduced.

Within another aspect, peptide analogues are provided comprising at least seven amino acids selected from residues 86 to 99 of human myelin basic protein, including residue 99, wherein L-proline at position 99 is altered to another amino acid, the peptide analogue having increased MHC binding relative to MBP 87–99. Within one embodiment, L-proline at position 99 is altered to a D-amino acid such as D-alanine, D-arginine, D-asparagine, D-aspartic acid, D-cysteine, D-glutamine, D-glutamic acid, D-glycine, D-histidine, D-isoleucine, D-leucine, D-lysine, D-methionine, D-phenylalanine, D-proline, D-serine, D-threonine, D-tryptophan, D-tyrosine or D-valine. Within another embodiment, the N-terminal amino acid and/or C-terminal amino acids of the peptide analogue are altered to a D-amino acid, such that upon administration of the peptide analogue in vivo proteolysis is reduced.

Within another aspect, peptide analogues are provided comprising at least seven amino acids selected from residues 86 to 99 of human myelin basic protein, including residue 97, wherein L-arginine at position 97 is altered to another amino acid, the peptide analogue having increased MHC binding relative to MBP 87–99. Within one embodiment, L-arginine at position 97 is altered to a D-amino acid such as D-alanine, D-arginine, D-asparagine, D-aspartic acid, D-cysteine, D-glutamine, D-glutamic acid, D-glycine, D-histidine, D-isoleucine, D-leucine, D-lysine, D-methionine, D-phenylalanine, D-proline, D-serine, D-threonine, D-tryptophan, D-tyrosine or D-valine. Within another embodiment, the N-terminal amino acid and/or C-terminal amino acids of the peptide analogue are altered to a D-amino acid, such that upon administration of the peptide analogue in vivo proteolysis is reduced.

Within other aspects of the present invention, pharmaceutical compositions are provided comprising any of the above-described peptide analogues in combination with a pharmaceutically acceptable carrier or diluent. Further, methods are provided for treating multiple sclerosis, comprising administering to a patient a therapeutically effective amount of any of the above-described peptide analogues or pharmaceutical compositions.

These and other aspects of the invention will become evident upon reference to the following detailed description and attached drawings. In addition, various references are set forth below which describe in more detail certain procedures or compositions. Each of these references are incorporated herein by reference in their entirety as if each were individually noted for incorporation.

BRIEF DESCRIPTION OF THE DRAWINGS

FIG. 1 depicts DNA and predicted amino acid sequence for human myelin basic protein (SEQ ID NOs: 1 and 2 respectively).

FIG. 2 graphically depicts the inhibition of 10 $\mu$M biotinylated MBP 86–99 binding to rat spleen cells by no inhibitor (□), 200 $\mu$M Sperm Whale Myoglobin ("SWM") (■), 50 $\mu$M h88 (■), and 50 $\mu$M MBP 87–99 (▨).

FIGS. 3A and 3B graphically depict the proliferative response, in two separate experiments, of lymph node cells obtained from MBP 87–99 immunized rats.

FIG. 4 graphically depicts the proliferative response of lymph node cells obtained from h88 immunized rats.

FIGS. 5A, 5B, 5C and 5D graphically depict the proliferative response of a rat MBP 87–99 reactive T cell line to MBP 87–99, control peptide, and peptide analogues with D-amino acid substitutions at residues 87, 88, 98 and 99, respectively.

FIGS. 6A, 6B and 6C graphically depict the results of treatment, in three separate experiments with a h88 peptide analog, after MBP 87–99 induced EAE.

FIG. 7 graphically depicts induction of EAE in rats injected with Complete Freund's Adjuvant ("CFA") containing MBP 87–99 or h88.

FIGS. 8A and 8B depict the proliferative response of lymph node cells obtained from MBP (87–99) immunized and A97 immunized SJL mice.

FIG. 9 graphically depicts the proliferative response of murine T cell clones to MBP 87–99 and A97.

FIG. 10 graphically depicts the results of treatment with A97 following induction of EAE in SJL mice.

FIG. 11 graphically depicts the induction of EAE in SJL mice following a single injection of MBP 87–99 or A97.

FIG. 12 graphically depicts apoptosis in an MBP 87–99 reactive T cell line upon treatment with an anti-CD3 monoclonal antibody, MBP 87–99, 97A, neurotensin or PLP (myelin proteolipid-protein).

FIG. 13 depicts phosphorylation of the CD3 zeta chain in a T cell line following treatment with MBP 87–99, 91A, or 97A.

DETAILED DESCRIPTION OF THE INVENTION

Figure 2:
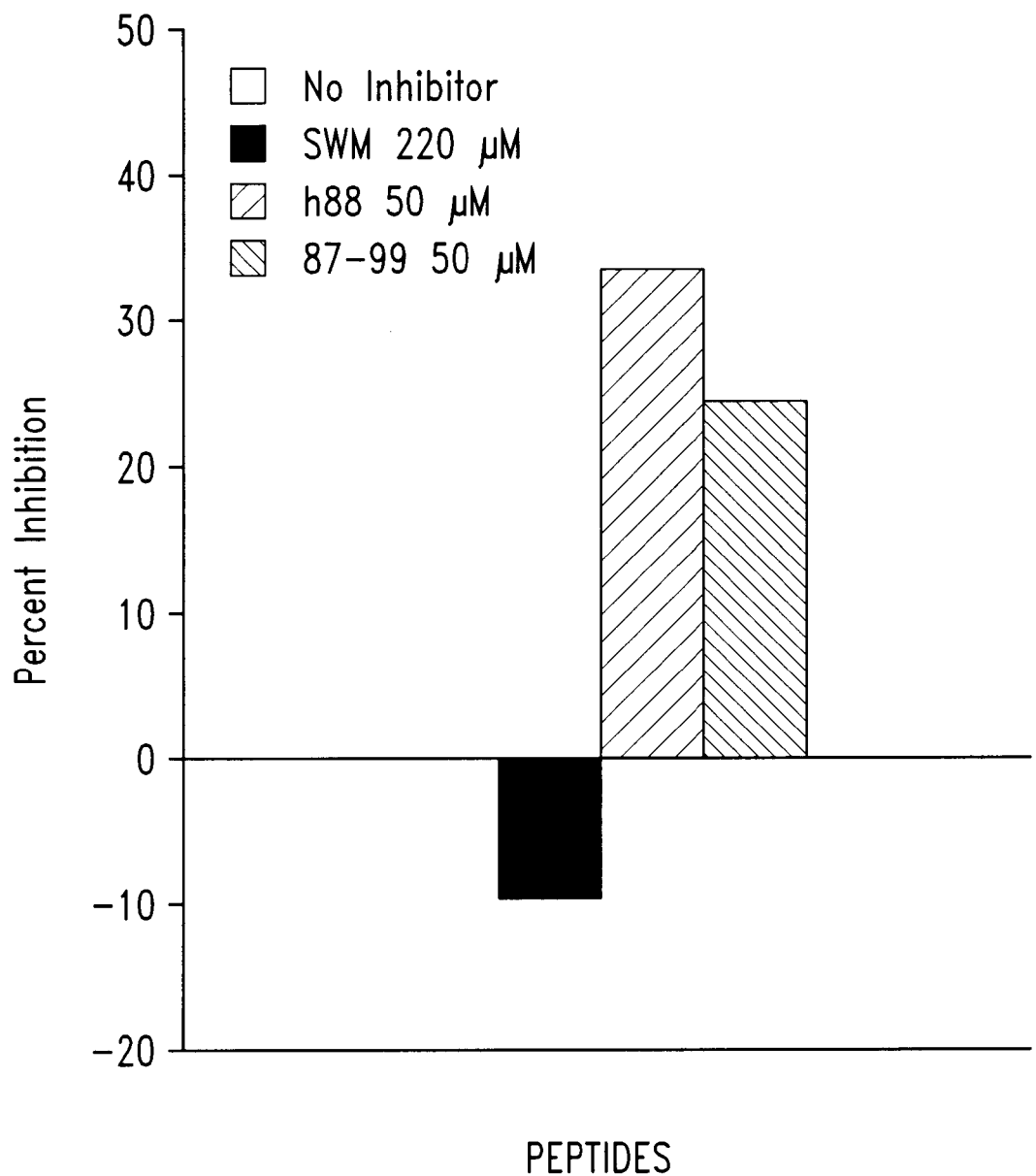
Figure 3A:
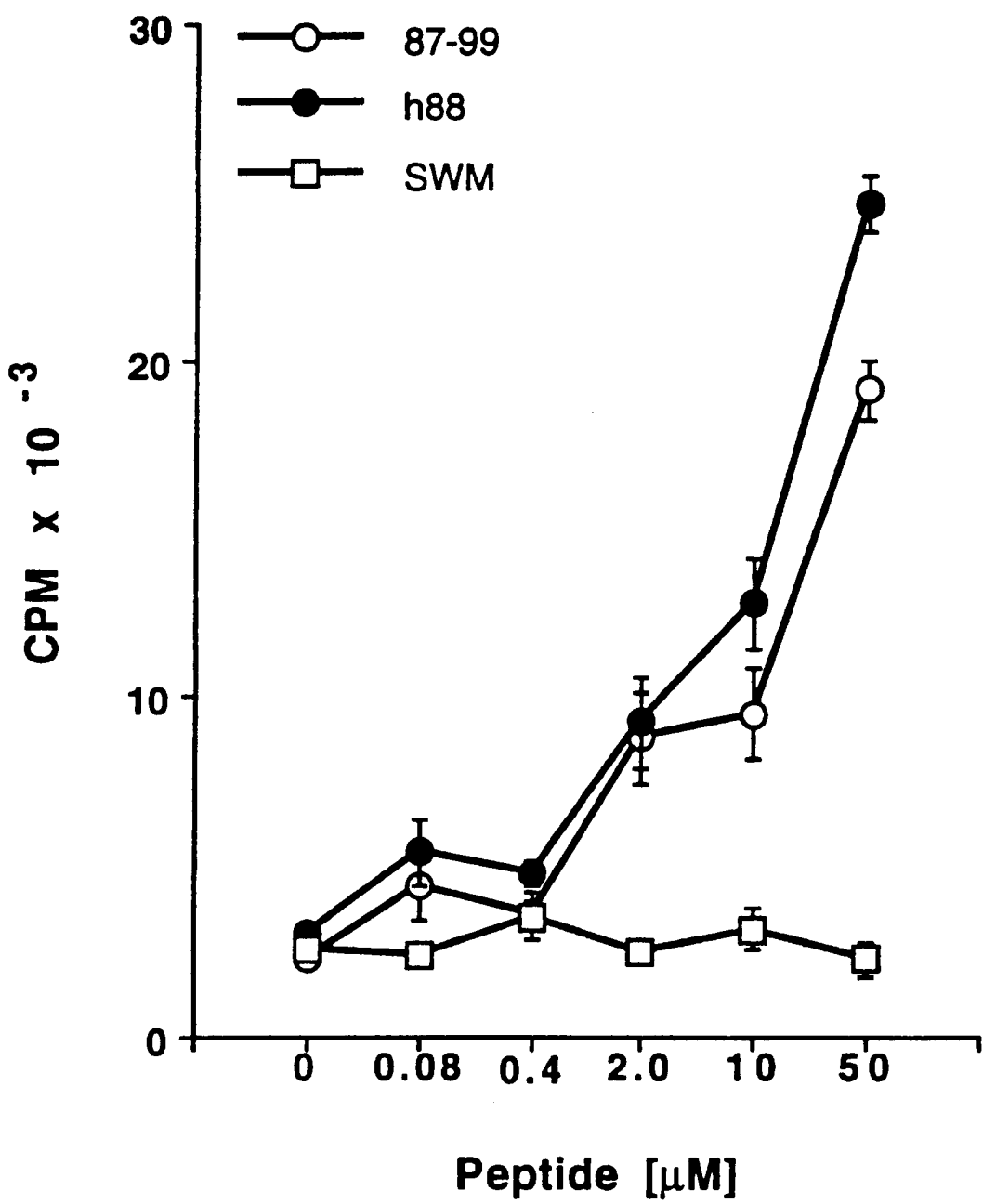
Figure 3B:
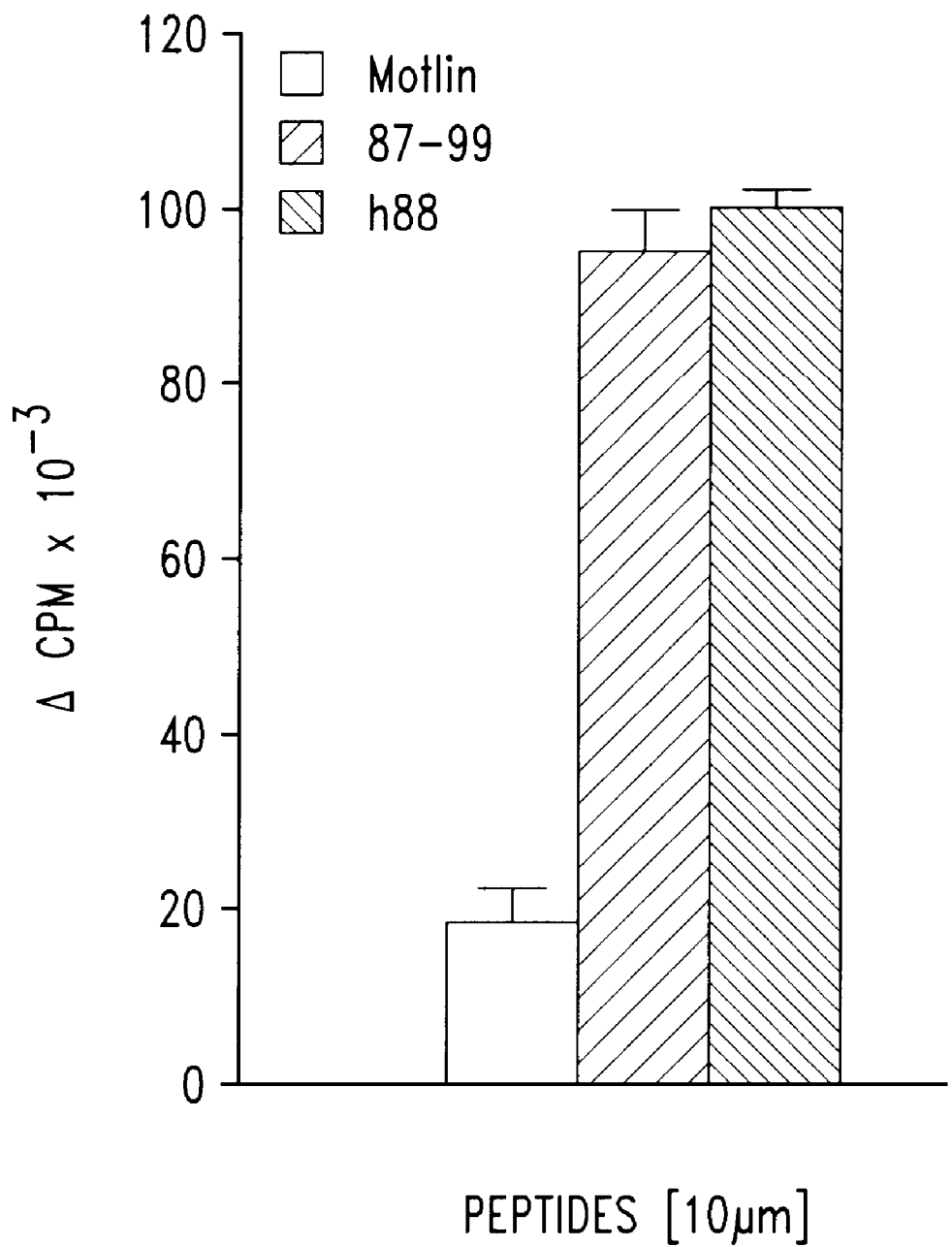

Prior to setting forth the invention, it may be helpful to an understanding thereof to set forth definitions of certain terms that will be used hereinafter.

"Human myelin basic protein" ("MBP") refers to a protein found in the cytoplasm of human oligodendroglial cells. The nucleotide sequence and predicted amino acid sequence of human MBP are presented in FIG. 1 (SEQ. ID Nos. 1 and 2). Although not depicted in FIG. 1, different molecular forms of human myelin basic protein generated by differential splicing or post-translational modification as well as bacterial or viral sequences which have T-cell cross-reactivity, and which mimic human myelin basic protein, are also considered to be within the scope of the present invention.

"Peptide analogues" of myelin basic protein are at least 7 amino acids in length and contain at least one difference in amino acid sequence between the analogue and native human myelin basic protein, at least one of which is a difference at residue 87, 88, 97, 98 or 99. Unless otherwise indicated, a named amino acid refers to the L-form. An L-amino acid from the native peptide may be altered to another one of the 20 L-amino acids commonly found in proteins, to any one of the 20 D-amino acids commonly found in proteins, to a rare amino acid, such as 4-hydroxyproline or hydroxylysine, or to a non-protein amino acid such as β-alanine and homoserine. Also included with the scope of the present invention are amino acids which have been altered by chemical means such as methylation (e.g, β-methylvaline), amidation of the C-terminal amino acid by an alkylamine such as ethylamine, ethanolamine, and ethylene diamine, and acylation or methylation of an amino acid side chain function (e.g., acylation of the epsilon amino group of lysine).

"Residue 87," "residue 88," "residue 97," "residue 98" and "residue 99" (also called position 87, position 88, position 97, position 98 and position 99, respectively), refer to amino acids 87, 88, 97, 98 and 99 of human myelin basic protein as displayed in FIG. 1, or an amino acid at a comparative position. Briefly, the numbering system for these residues relates to the amino acid position within the native human protein, regardless of the length of the peptide or the amino acid position within that peptide. When a letter precedes the residue number (e.g., A97), it refers to the amino acid (in one-letter code) at that residue. A capital letter refers to the L-form of the amino acid; a lower case letter refers to the D-form of the amino acid.

Peptide Analogues of Myelin Basic Protein

As noted above, the present invention provides peptide analogues comprising at least 7 amino acids selected from residues 86–99 of human myelin basic protein and including an alteration of the naturally occurring L-valine at position 87, L-histidine at position 88, L-arginine at position 97, L-threonine at position 98, or L-proline at position 99 to another amino acid. In addition to such single alterations, other amino acids within residues 86–99 of human myelin basic protein may also be altered, with the exception of residues 91, 95 and 97. In related aspects, the peptide analogues provided herein may additionally have either (or both) the N-terminal and C-terminal residues altered to an amino acid such that proteolysis or degradation is reduced upon administration to a patient compared to a peptide analogue without these additional alterations. Peptide analogues as disclosed herein may be utilized in a variety of in vitro assays as discussed below, as well as for the treatment of multiple sclerosis.

As noted above, any amino acid substitution at position 87 is within the scope of this invention. Preferred peptide analogues include those wherein L-valine is altered to a D-amino acid, including any one of the following amino acids: D-alanine, D-arginine, D-asparagine, D-aspartic acid, D-cysteine, D-glutamine, D-glutamic acid, D-glycine, D-histidine, D-isoleucine, D-leucine, D-lysine, D-methionine, D-phenylalanine, D-proline, D-serine, D-threonine, D-tryptophan, D-tyrosine and D-valine. These amino acids include both conservative (similar charge, polarity, hydrophobicity, and bulkiness) and non-conservative amino acids. Although typically one might expect that only non-conservative amino acid alterations would provide a therapeutic effect, unexpectedly even conservative changes affect the function of the peptide analogue as compared to the native peptide. Such diversity of substitution is further illustrated by the fact that the amino acids noted above are hydrophobic and hydrophilic, charged and uncharged, polar and non-polar.

Similarly, any amino acid substitution at residue 88, residue 97, residue 98, or residue 99 is also within the scope of this invention. Preferred peptide analogues contain alterations of L-histidine (residue 88), L-arginine (residue 97), L-threonine (residue 98), or L-proline (residue 99) to a D-amino acid, including to any one of the following amino acids: D-alanine, D-arginine, D-asparagine, D-aspartic acid, D-cysteine, D-glutamine, D-glutamic acid, D-glycine, D-histidine, D-isoleucine, D-leucine, D-lysine, D-methionine, D-phenylalanine, D-proline, D-serine, D-threonine, D-tryptophan, D-tyrosine and D-valine.

As noted above, within certain aspects of the present invention, the peptide analogues provided herein may have more than one amino acid alteration in residues 86–99. Representative examples of such peptide analogues include those which have a D-amino acid substituted in residues 87 and 98, 87 and 99, 88 and 98, or 88 and 99. Also included within the scope of the invention are peptide analogues with triple D-amino acid substitutions (e.g., a substitution of D-amino acids in residues 87, 98 and 99; a substitution of D-amino acids in residues 88, 98 and 99; a substitution of D-amino acids in residues 87, 88 and 98; and a substitution of a D-amino acid in residues 87, 88 and 99), and quadruple substitutions (e.g., the substitution of a D-amino acid in residues 87, 88, 98 and 99).

Peptide analogues of the present invention are preferably 7 to 16 amino acids in length, and usually not longer than 33 amino acids (e.g., residues 84–106). Particularly preferred peptide analogues are 14 amino acids in length. Such peptide analogues may be readily synthesized by standard chemical techniques given the disclosure provided herein. In general, peptide analogues may be prepared by solid-phase peptide synthesis methodology which involves coupling each protected amino acid residue to a resin support, preferably a 4-methyl-benzhydrylamine resin, by activation with dicyclohexylcarbodiimide to yield a peptide with a C-terminal amide. Alternatively, a chloromethyl resin (Merrifield resin)

may be used to yield a peptide with a free carboxylic acid at the C-terminus. Side-chain functional groups are protected as follows: benzyl for serine, threonine, glutamic acid, and aspartic acid; tosyl for histidine and arginine; 2-chlorobenzyloxycarbonyl for lysine and 2,6-dichlorobenzyl for tyrosine. Following coupling, the t-butyloxycarbonyl protecting group on the alpha amino function of the added amino acid is removed by treatment with trifluoroacetic acid followed by neutralization with di-isopropyl-ethylamine. The next protected residue is then coupled onto the free amino group, propagating the peptide chain. After the last residue has been attached, the protected peptide-resin is treated with hydrogen fluoride to cleave the peptide from the resin, as well as deprotect the side chain functional groups. Crude product can be further purified by gel filtration, HPLC, partition chromatography, or ion-exchange chromatography.

Peptide analogues within the present invention should (1) have comparable, or preferably, increased binding to MHC as compared to MBP (87–99); (2) cause proliferation of a MBP (87–99)-reactive T cell line; (3) inhibit induction of experimental allergic encephalomyelitis (EAE) by MBP (87–99) in rodents; and (4) elicit specific T cell responses in rodents upon immunization.

Thus, candidate peptide analogues may be screened for their ability to treat MS by (1) an assay measuring competitive binding to MHC, (2) an assay measuring a T cell proliferation, (3) an assay assessing inhibition of induction of EAE, and (4) an assay which measures specific T cell responses. Those analogues that inhibit binding of the native peptides, stimulate proliferation of MBP-reactive cell lines, and inhibit the development of EAE by native human MBP (87–99), may be useful as therapeutics. Although not essential, a further assay may be performed to examine whether the analogue induces EAE when injected with an adjuvant.

The binding of peptide analogues to MHC class II molecules (as compared to MBP 87–99) may be assayed in a variety of manners, including, for example, on whole cells. For example, within one embodiment, Lewis rat spleen cells are cultured for 3 hours to allow adherent cells to adhere to polystyrene petri dishes. Non-adherent cells are removed. Adherent cells, which contain cells expressing MHC Class II molecules, are collected by scraping the dishes. The binding of peptide analogues to cells may then be measured by, for example, a cytofluorometric assay. In such assays, splenic adherent cells are mixed with different concentrations of peptide analogues and incubated for 1 hour at 37° C. in a $CO_2$ incubator. Following incubation, biotin-labeled MBP (87–99) is added to the culture wells. The cells are incubated for another hour and then washed three times in medium. Phycoerythrin-conjugated or fluorescein-conjugated streptavidin is then added along with a fluorochrome-labeled OX-6 or OX-17 monoclonal antibody, which reacts with rat MHC class II I-A and I-E, respectively. The cells are washed twice before analysis by flow cytometry. Fluorescence intensity is calculated by subtracting the fluorescence value obtained from cells stained with phycoerythrin-streptavidin alone (control staining) from the fluorescence value obtained from biotin-labeled MBP (87–99) plus phycoerythrin-streptavidin (experimental staining). Staining without analogue establishes a 100% value. Percent inhibition is calculated for each analogue and expressed as $IC_{50}$ values. A peptide analogue which is comparable to native peptide, or more potent (e.g., an $IC_{50}$ value of less than 100 μM), is suitable for further screenings.

Candidate peptide analogues are further tested for their ability to cause proliferation of T cell lines. Two different assays may be used as alternatives. The first measures the ability of the analogue to cause proliferation of a T cell line, and the second measures the ability of the peptide analogue to cause proliferation in primary immune lymph node cells.

In the direct proliferation assay, MBP (87–99) reactive T cell lines may be used as target cells. T cell lines are established from lymph nodes taken from rats or mice injected with MBP (87–99). Lymph node cells are isolated and cultured for 5 to 8 days with MBP (87–99) and IL-2. Viable cells are recovered and a second round of stimulation is performed with MBP (87–99) and irradiated splenocytes as a source of growth factors. After 5 to 6 passages in this manner, the proliferative potential of the cell lines are determined. MBP-reactive lines are used in the proliferation assay. In this assay, T cell lines are cultured for three days with various concentrations of peptide analogues and irradiated, autologous splenocytes. After three days, 0.5–1.0 μCi of [$^3$H]-thymidine is added for 12–16 hours. Cultures are harvested and incorporated counts determined. Mean CPM and standard error of the mean are calculated from triplicate cultures.

Within the second assay, draining lymph node cells from Lewis rats or SJL mice injected with MBP (87–99) may be used. Preferably, this assay is used in combination with the proliferation assay using T cell lines. Briefly, Lewis rats or SJL mice are injected subcutaneously with MBP (87–99) peptide in complete Freund's adjuvant. Nine to ten days later, draining lymph node cells are isolated and single-cell suspensions are prepared. Lymph node cells are incubated with various concentrations of peptide analogues for three days in a humidified air chamber containing 6.5% $CO_2$. After incubation, the cultures are pulsed with 1–2 μCi of [$^3$H]-thymidine for 12–18 hours. Cultures are harvested on fiberglass filters and counted in a scintillation counter. Mean CPM and the standard error of the mean are calculated from data determined in triplicate cultures. Peptide analogues yielding results that are more than three standard deviations of the mean response with a comparable concentration of MBP (87–99) are considered non-stimulatory. Peptide analogues which are suitable for further screening will preferably, at concentrations of at least 10 μM, cause stimulation to a level of at least 25% of the native peptide.

Candidate peptides, which have comparable or increased binding to MHC as compared to MBP (87–99) and which cause proliferation of a T cell line or primary lymph node cells, are further tested for their ability to inhibit the induction of EAE by MBP (87–99). Briefly, 500 μg of MBP (87–99) is injected as an emulsion in complete Freund's adjuvant supplemented with heat killed *Mycobacterium tuberculosis* (H37Ra). Rats are injected subcutaneously at the base of the tail with 200 μl of the emulsion. Rats are divided into two groups. Approximately 2 days prior to disease induction (usually 10 days following injection of MBP (87–99)) rats are injected intraperitoneally either with PBS or peptide analogues in PBS. Mice may also be used to test inhibition of induction of EAE. Animals are monitored for clinical signs on a daily basis by an observer blind to the treatment protocol. EAE in rats is scored on a scale of 0–4: 0, clinically normal; 1, flaccid tail paralysis; 2, hind limb weakness; 3, hind limb paralysis; 4, front and hind limbs affected. Peptide analogues injected at 5 mg/kg or less (approximately 1 mg per rat) are considered to inhibit the development of EAE if there is a 50% reduction in the mean cumulative score over seven days following onset of disease symptoms in the control group.

Candidate peptide analogues may also be assayed for their ability to elicit antigen specific T cell responses in rodents utilizing methods essentially described by Gaur et al., *Science* 258:1491–1494, 1992; Offner et al., *J. Immunol.* 148:1706, 1992; Gold et al., *J. Immunol.* 148:1712, 1992; Karin et al., *J Exp. Med.* 18:2227–2237, 1994. For example, within one embodiment an initial 1:10 dilution of a 1.5 mM stock solution of MBP (87–99) or peptide analogue is added into tissue culture medium. Samples are then diluted by three-fold serial dilutions (final volume 100 $\mu$l). T cell lines prepared as described in Example 3 below, are resuspended to $4\times10^5$ cells per ml and 50 $\mu$l aliquots added to each well ($5\times10^4$ cells per well). Approximately $1\times10^6$ irradiated (3000R) splenocyte feeder cells are also added to each well. Cultures are incubated at 37° C. in humidified air containing 7.5% $CO_2$ for 3 days, and twelve to sixteen hours prior to harvesting 0.5–1.0 $\mu$Ci of [$^3$H]-thymidine (20 Ci/mM; New England Nuclear) is added to each well and the cultures reincubated. Plates are harvested with a Matrix filtermate harvester (Packard) and counted using an Automatic Direct Beta Counter (Packard). Mean cpm and the standard error of the mean are calculated from triplicate wells. Peptide analogues which cause proliferation at concentrations of greater than 5 $\mu$M peptide analogue, as compared to unimmunized animals, may be utilized for the treatment of MS as described below.

Other suitable assays of antigen-specific T cell responses include induction of cytokine production, phosphorylation of the CD3 zeta chain, and induction of apoptosis. Briefly, for assaying cytokine production, an IL-2-stimulated T cell line, which is reactive to MBP 87–89, is incubated with IL-2 and various MBP peptide analogues. Cytokine release is measured at 48 hr. Cytokines are measured by ELISA, or alternatively, RNA expression of cytokines may be measured by Northern blot, RNase probe protection or other standard hybridization methods. Cytokines to be assayed include IL-1 through IL-14, $\gamma$-IFN, TNF, and the like. Phosphorylation of the CD3 zeta chain is assayed in MBP 87–89-specific T cells. Briefly, cells are co-incubated with antigen-presenting cells, such as T-depleted splenocytes, which have been pulsed with MBP 87–99 or peptide analogue. Cells are then lysed, and the zeta chain is immunoprecipitated and electrophoresed on an SDS-PAGE gel. The phosphorynosine may be detected with an antibody. In a third assay, apoptosis may be induced in an antigen-specific manner. For this assay, an MBP stimulated T cell line is incubated with IL-2 and various peptides. Cell loss is measured by flow cytometry or other standard method.

In addition to the above described assays, suitable peptide analogues may also be tested for direct induction of EAE. For example, as described in Examples 6 and 8, various amounts of peptide analogues with adjuvant are injected at the base of the tail of a rat, and the rat examined daily for signs of EAE. A peptide analogue that is not considered to cause EAE has a mean cumulative score of less than or equal to 1 over seven days when 1 mg of peptide analogue (5 mg/kg) in CFA is injected. Suitable peptide analogues, however, may induce EAE (i.e., have a mean cumulative score of greater than 1 over seven days) when 1 mg of peptide analogue (5 mg/kg) is administered in adjuvant.

Treatment and Prevention of Multiple Sclerosis

As noted above, the present invention provides methods for treating and preventing multiple sclerosis by administering to the patient a therapeutically effective amount of a peptide analogue of human myelin basic protein as described herein. Patients suitable for such treatment may be identified by criteria establishing a diagnosis of clinically definite MS as defined by the workshop on the diagnosis of MS (Poser et al., *Ann. Neurol.* 13:227, 1983). Briefly, an individual with clinically definite MS has had two attacks and clinical evidence of either two lesions or clinical evidence of one lesion and paraclinical evidence of another, separate lesion. Definite MS may also be diagnosed by evidence of two attacks and oligoclonal bands of IgG in cerebrospinal fluid or by combination of an attack, clinical evidence of two lesions and oligoclonal band of IgG in cerebrospinal fluid. Slightly lower criteria are used for a diagnosis of clinically probable MS.

Effective treatment of multiple sclerosis may be examined in several different ways. Satisfying any of the following criteria evidences effective treatment. Three main criteria are used: EDSS (extended disability status scale), appearance of exacerbations or MRI (magnetic resonance imaging).

The EDSS is a means to grade clinical impairment due to MS (Kurtzke, *Neurology* 33:1444, 1983). Eight functional systems are evaluated for the type and severity of neurologic impairment. Briefly, prior to treatment, patients are evaluated for impairment in the following systems: pyramidal, cerebella, brainstem, sensory, bowel and bladder, visual, cerebral, and other. Follow-ups are conducted at defined intervals. The scale ranges from 0 (normal) to 10 (death due to MS). A decrease of one full step defines an effective treatment in the context of the present invention (Kurtzke, *Ann. Neurol.* 36:573–79, 1994).

Exacerbations are defined as the appearance of a new symptom that is attributable to MS and accompanied by an appropriate new neurologic abnormality (IFNB MS Study Group, supra). In addition, the exacerbation must last at least 24 hours and be preceded by stability or improvement for at least 30 days. Briefly, patients are given a standard neurological examination by clinicians. Exacerbations are either mild, moderate, or severe according to changes in a Neurological Rating Scale (Sipe et al., *Neurology* 34:1368, 1984). An annual exacerbation rate and proportion of exacerbation-free patients are determined. Therapy is deemed to be effective if there is a statistically significant difference in the rate or proportion of exacerbation-free patients between the treated group and the placebo group for either of these measurements. In addition, time to first exacerbation and exacerbation duration and severity may also be measured. A measure of effectiveness as therapy in this regard is a statistically significant difference in the time to first exacerbation or duration and severity in the treated group compared to control group.

MRI can be used to measure active lesions using gadolinium-DTPA-enhanced imaging (McDonald et al. *Ann. Neurol.* 36:14, 1994) or the location and extent of lesions using $T_2$-weighted techniques. Briefly, baseline MRIs are obtained. The same imaging plane and patient position are used for each subsequent study. Positioning and imaging sequences are chosen to maximize lesion detection and facilitate lesion tracing. The same positioning and imaging sequences are used on subsequent studies. The presence, location and extent of MS lesions are determined by radiologists. Areas of lesions are outlined and summed slice by slice for total lesion area. Three analyses may be done: evidence of new lesions, rate of appearance of active lesions, percentage change in lesion area (Paty et al., *Neurology* 43:665, 1993). Improvement due to therapy is established when there is a statistically significant improvement in an individual patient compared to baseline or in a treated group versus a placebo group.

Candidate patients for prevention may be identified by the presence of genetic factors. For example, a majority of MS patients have HLA-type DR2a and DR2b. The MS patients having genetic dispositions to MS who are suitable for treatment fall within two groups. First are patients with early disease of the relapsing remitting type. Entry criteria would include disease duration of more than one year, EDSS score of 1.0 to 3.5, exacerbation rate of more than 0.5 per year, and free of clinical exacerbations for 2 months prior to study. The second group would include people with disease progression greater than 1.0 EDSS unit/year over the past two years.

Efficacy of the peptide analogue in the context of prevention is judged based on at least one of the following criteria: frequency of MBP reactive T cells determined by limiting dilution, proliferation response of MBP reactive T cell lines and clones, cytokine profiles of T cell lines and clones to MBP established from patients. Efficacy is established by decrease in frequency of reactive cells, a reduction in thymidine incorporation with altered peptide compared to native, and a reduction in TNF and IFN-α. Clinical measurements include the relapse rate in one and two year intervals, and a change in EDSS, including time to progression from baseline of 1.0 unit on the EDSS which persists for six months. On a Kaplan-Meier curve, a delay in sustained progression of disability shows efficacy. Other criteria include a change in area and volume of T2 images on MRI, and the number and volume of lesions determined by gadolinium enhanced images.

Peptide analogues of the present invention may be administered either alone, or as a pharmaceutical composition. Briefly, pharmaceutical compositions of the present invention may comprise one or more of the peptide analogues described herein, in combination with one or more pharmaceutically or physiologically acceptable carriers, diluents or excipients. Such compositions may comprise buffers such as neutral buffered saline, phosphate buffered saline and the like, carbohydrates such as glucose, mannose, sucrose or dextrans, mannitol, proteins, polypeptides or amino acids such as glycine, antioxidants, chelating agents such as EDTA or glutathione, adjuvants (e.g., aluminum hydroxide) and preservatives. In addition, pharmaceutical compositions of the present invention may also contain one or more additional active ingredients, such as, for example, cytokines like β-interferon.

Compositions of the present invention may be formulated for the manner of administration indicated, including for example, for oral, nasal, venous, intracranial, intraperitoneal, subcutaneous, or intramuscular administration. Within other embodiments of the invention, the compositions described herein may be administered as part of a sustained release implant. Within yet other embodiments, compositions of the present invention may be formulized as a lyophilizate, utilizing appropriate excipients which provide stability as a lyophilizate, and subsequent to rehydration.

Pharmaceutical compositions of the present invention may be administered in a manner appropriate to the disease to be treated (or prevented). The quantity and frequency of administration will be determined by such factors as the condition of the patient, and the type and severity of the patient's disease. Within particularly preferred embodiments of the invention, the peptide analogue or pharmaceutical compositions described herein may be administered at a dosage ranging from 5 to 50 mg/kg, although appropriate dosages may be determined by clinical trials. Patients may be monitored for therapeutic effectiveness by MRI, EDSS, and signs of clinical exacerbation, as described above.

The following examples are offered by way of illustration and not by way of limitation.

EXAMPLE 1

PREPARATION OF PEPTIDES

The peptides are synthesized by solid phase methodology on a peptide synthesizer (Beckman model 990). Peptides with an amidated carboxyl-terminus are prepared with a p-methylbenzhydrylamine resin (MBHA resin); for peptides with a free carboxyl-terminus, a Merrifield resin coupled with the appropriately protected amino acid is used. Both resins are obtained from Bachem Fine Chemicals (Torrance, Calif.). Derivatized amino acids (Bachem Fine Chemicals) used in the synthesis are of the L-configuration unless specified otherwise, and the N-alpha-amino function protected exclusively with the t-butyloxycarbonyl group. Side-chain functional groups are protected as follows: benzyl for serine, threonine, glutamic acid, and aspartic acid; tosyl for histidine and arginine; 2-chlorobenzyloxycarbonyl for lysine and 2,6-dichlorobenzyl for tyrosine. Coupling of the carboxyl-terminal amino acid to the MBHA resin is carried out with dicyclohexylcarbodiimide and the subsequent amino acids are coupled with dicyclohexylcarbodiimide according to Ling et al. (*Proc. Natl. Acad. Sci. USA* 81:4302, 1984). After the last amino acid is incorporated, the t-butyoxycarbonyl protecting group is removed and the peptide-resin conjugate treated with a mixture of 14 ml hydrofluoric acid (HF), 1.4 ml anisole, and 0.28 ml methylethyl sulfide per gram of resin conjugate at −20° C. for 0.5 hr and at 0° C. for 0.5 hr. HF is removed in vacuum at 0° C., and the resulting peptide and resin mixture is washed twice with diethyl ether and twice with chloroform and diethyl ether alternately. The peptide is extracted five times with 2 M acetic acid, and the extract lyophilized. The lyophilized product is first purified on a column of Sephadex G-25 fine (Pharmacia-LKB, Piscataway, N.J.) developed in 30% acetic acid to remove the truncated fragments and inorganic salts (Ling et al., 1984). Next, peptides are further purified by CM-32 carboxymethylcellulose cation-exchange chromatography (Ling et al., 1984). Final purification is achieved by partition chromatography on Sephadex G-25 fine (Ling et al., 1984). The synthetic product is characterized by amino acid analysis, mass spectrometric analysis, and reversed-phase HPLC.

One peptide analogue, which is prepared in the above manner, consists of amino acids 86–99 of human myelin basic protein, with the exception that L-histidine at residue 88 is altered to D-histidine. This peptide analogue is referred to hereinafter as "h88". Another peptide analogue consists of amino acids 86–99 of human MBP, except that L-arginine at residue 97 is altered to L-alanine. This peptide analogue is referred to hereinafter as "A97."

EXAMPLE 2

MHC BINDING ASSAY

The ability of MBP peptides and peptide analogues to bind MHC is measured. An assay which characterizes the binding of peptides to MHC molecules on antigen presenting cells (APC) is employed (Mozes et al., *EMBO J.* 8:4049, 1989; Gautam et al., *PNAS* 91:767, 1994). Briefly, spleen cells are cultured in Dulbecco's modified Eagle's medium supplemented with 10% fetal bovine serum (Hyclone Laboratories, Logan, Utah) in standard polystyrene petri dishes (100×15 mm) in a 37° C. incubator containing 6.5% $CO_2$ for 3 hours. Thereafter, non-adherent cells are removed, and the plates are washed three times with PBS. Adherent cells are collected using a cell scraper. The binding of MBP (87–99) analogues is measured using a cytofluorometric assay. Briefly, $5 \times 10^5$ splenic adherent cells in staining buffer (PBS containing 0.1% bovine serum albumin) are mixed with different concentrations ranging from 0–400 μM of MBP (87–99) analogues in individual wells of U-shape 96-well microculture plates and incubated for 1 hr at 37° C.

in a 6.5% $CO_2$ incubator. Following incubation, 10 $\mu$M of biotin-labeled MBP (87–99) is added to culture wells for 1 h. Cells are washed three times with the staining buffer. Fluoroscein-conjugated streptavidin (Becton Dickinson, San Jose, Calif.) is added as a second step reagent (1 $\mu$g/well) along with 1 $\mu$g/well of fluorochrome-labeled OX-6 or OX-17 monoclonal antibody (Pharmingen, San Diego, Calif.), which reacts with rat MHC Class II I-A or I-E, respectively, and incubated for 20–30 minutes on ice. The cells are washed twice before cytofluorographic analysis on a FACScan (Becton Dickinson). Fluorescence intensity for each sample is calculated by subtracting the fluorescence obtained from OX positive cells stained with phycoerythrin-streptavidin alone (control staining) from the fluorescence obtained from OX positive cells stained with biotin-labeled MBP (87–99) plus phycoerythrin-streptavidin. Percent inhibition is calculated for each analogue and expressed as $IC_{50}$ values.

Results are shown in FIG. 2. Briefly, as can be seen in FIG. 2, h88 (50 $\mu$M) inhibits the binding of biotinylated MBP 86–99 to a greater extent than does MBP 87–99 (50 $\mu$M). Thus, it can be inferred that binding of h88 to MHC Class II molecules is greater than that of MBP 86–99. No inhibitor (□) and 200 $\mu$M SWM (■) have been shown as controls.

In addition, A97 inhibits binding of biotin-labeled MBP 86–99 to MHC assayed on adherent cells of SJL spleen.

EXAMPLE 3

LONG-TERM T CELL LINES

Antigen specific long-term T cell lines are derived using the method developed by Ben-Nun et al. (*Eur. J. Immunol.* 11:195, 1981). Briefly, Lewis rats are injected with MBP (87–99) as described above. Nine to ten days later draining lymph node cells are cultured ($10^7$/ml) for 5–8 days in stimulation medium together with 10–20 $\mu$M of the MBP (87–99) peptide and 15 $\mu$/ml IL-2. After 5 to 8 days of culture, viable cells are collected after Ficoll-Hypaque separation and washed three times. These cells are recultured at $1 \times 10^7$ cells/ml in medium with $5 \times 10^5$ irradiated (3000 rad) autologous splenocytes as accessory cells and 10–20 $\mu$M of MBP (87–99). After 5 to 6 stimulation cycles, plates are screened by the ability of cells to proliferate in response to MBP (87–99). Positive lines are transferred to 24-well flat bottom plates and restimulated. Antigen specific murine T cell lines may be generated in a similar manner.

EXAMPLE 4

ANTIGEN-SPECIFIC LYMPH NODE CELL PROLIFERATION ASSAY

Female Lewis rates, approximately six weeks old, are purchased from Harlan Sprague, Indianapolis, Ind. MBP peptides are dissolved in phosphate-buffered saline (PBS) and emulsified with an equal volume of complete Freund's adjuvant (Difco Laboratories, Inc., Detroit, Mich.) supplemented with 2 mg/ml of heat-killed *Mycobacterium tuberculosis* H37Ra in oil (Difco). Rats are immunized subcutaneously in the base of the tail with 0.1 ml containing 100 $\mu$g of the peptide (MBP 87–99 or h88) in the emulsion. Nine to ten days following immunization, rats are sacrificed, their draining lymph node removed, and a single cell suspension made. Cells are resuspended to $5 \times 10^6$ cells per ml in stimulation medium containing Dulbecco's modified Eagle's medium (Gibco BRL, Gaithersburg, Md.) supplemented with 2 mercaptoethanol ($5 \times 10^{-5}$ M), L-glutamine (2 mM), sodium pyruvate (1 mM), penicillin (100 $\mu$g/ml), streptomycin (100 $\mu$g/ml), and 1% normal rat serum.

For the assay, 100 $\mu$l of the lymph node cell suspension is added to 96-well flat-bottom wells in the presence of an equal volume of medium containing 10 $\mu$M of various peptides (including: motilin or Sperm Whale Myoglobin ("SWM") 110–121 as a negative control; MBP 87–99; and h88. Cultures are then incubated at 37° C. in humidified air containing 7.5% $CO_2$. After 3 days of incubation, 1.0 $\mu$Ci of tritiated thymidine (20 Ci/mM; New England Nuclear) is added to each well and the plates reincubated for an additional 12–16 hours. The plates are then harvested with a Matrix filtermate harvester (Packard) and counted using an Automatic Direct Beta Counter (Packard). Mean cpm and the standard error of the mean are calculated from triplicate wells.

Figure 4:
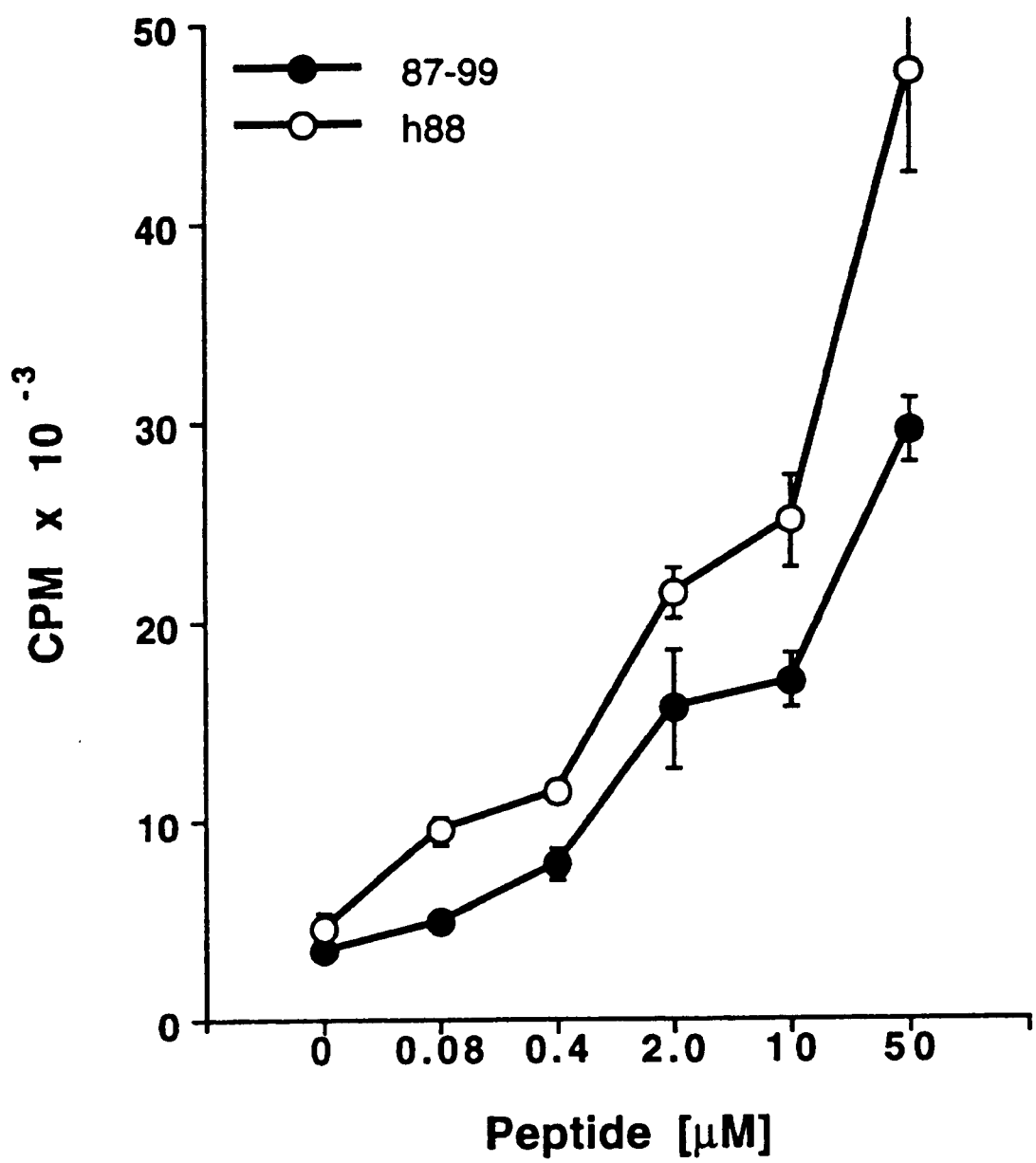
Figure 5A:
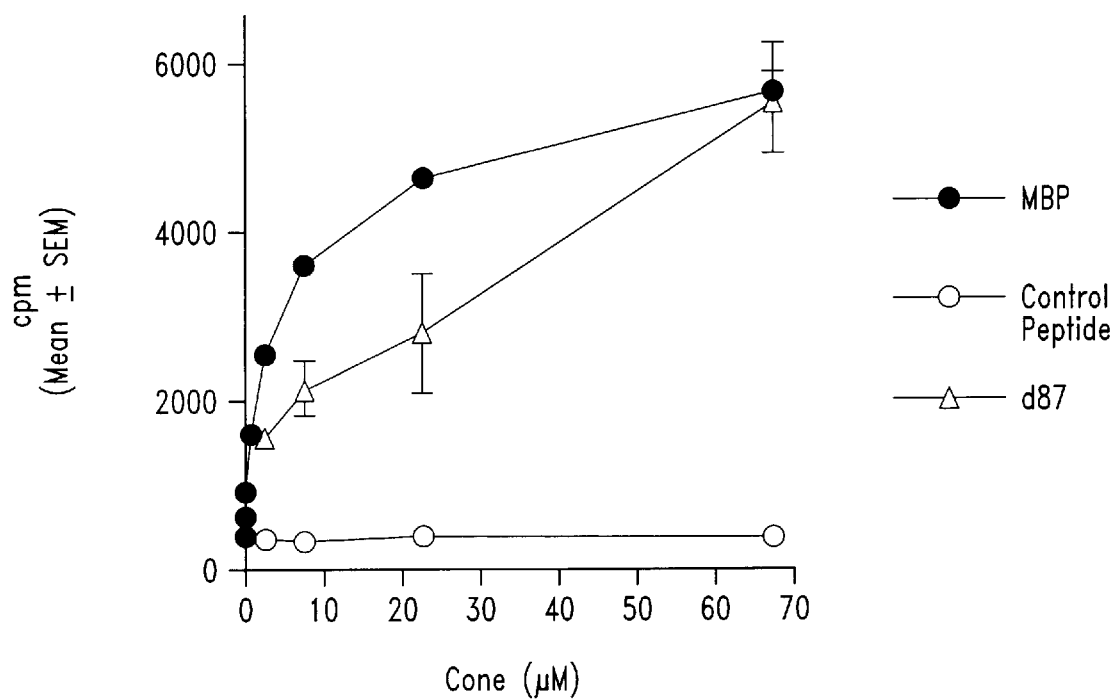
Figure 5B:
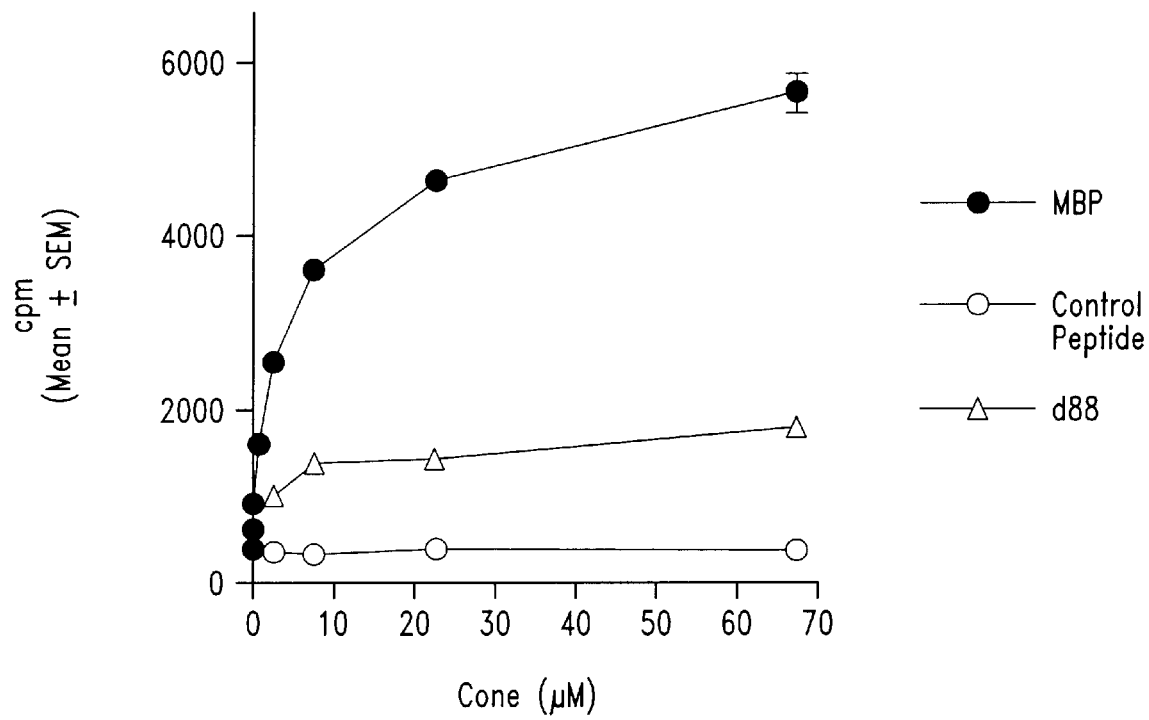
Figure 5C:
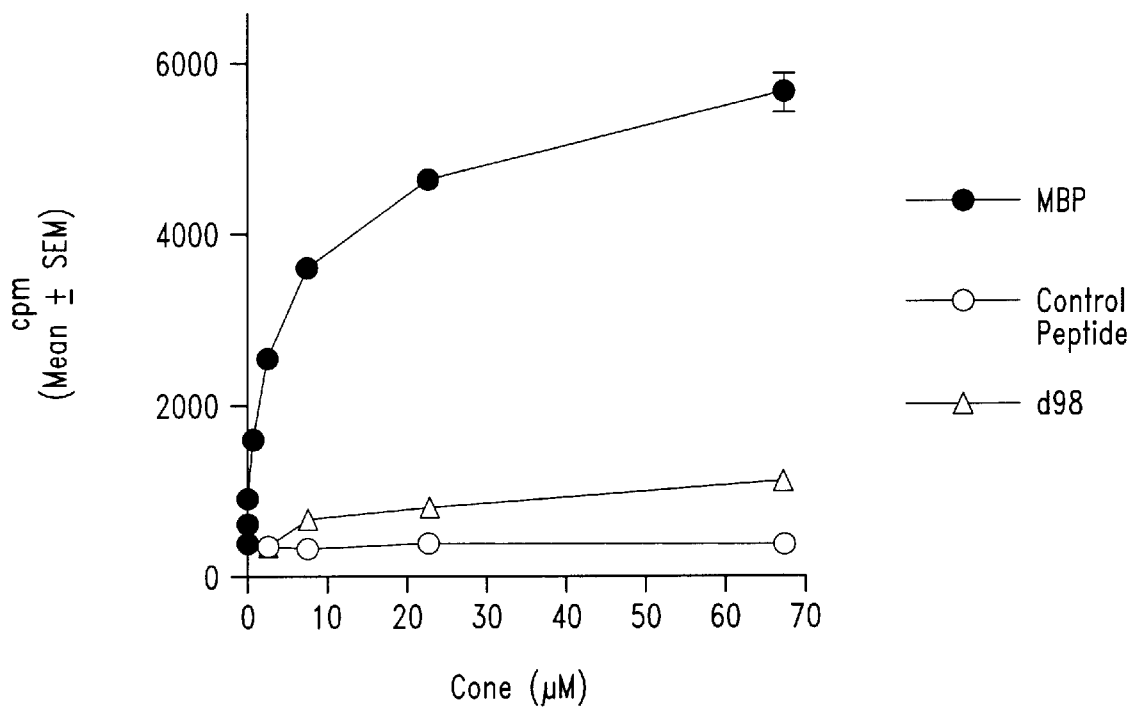
Figure 5D:
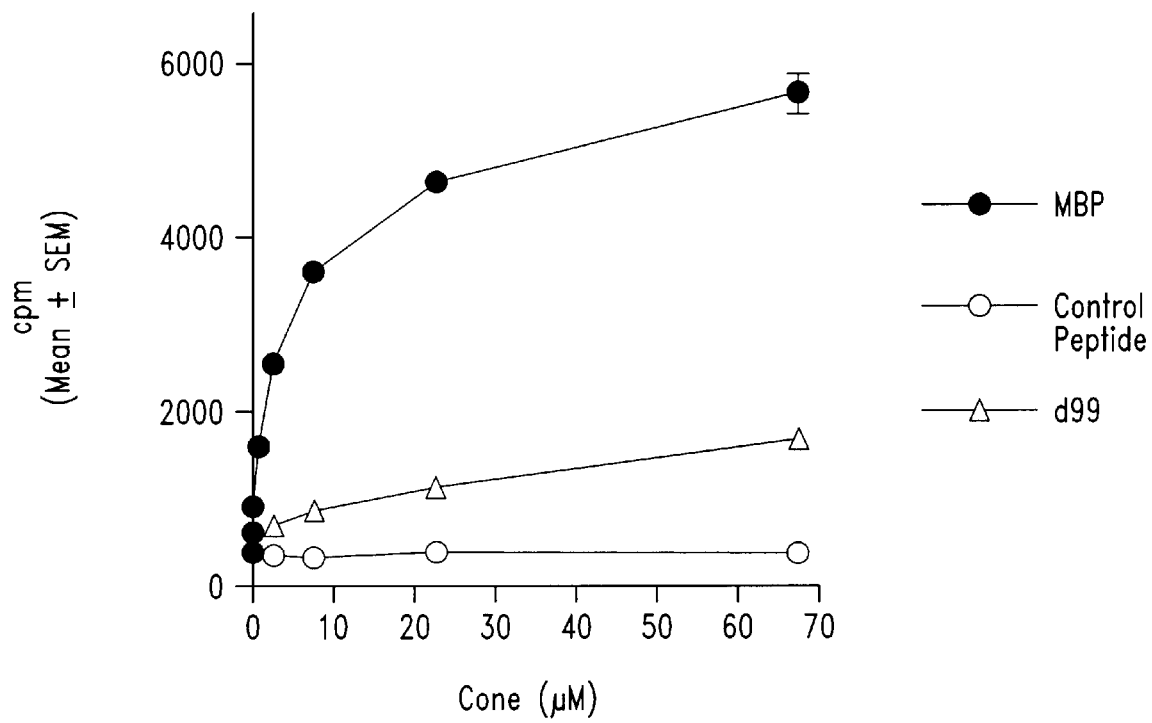

Results are provided in FIGS. 3A, 3B, 4, and 8. Briefly, as can be seen from FIGS. 3A and 3B, the proliferative response of lymph node cells from MBP 87–99 immunized rats was significant for both MBP 87–99 (○), and h88 (●), but not SWM (□) (see FIG. 3A). Similarly, in FIG. 3B the response was significant for both MBP 87–99 (■) and h88 (▨), but not motlin (□). In FIG. 4, the proliferative response of lymph node cells from h88 immunized rats is evident for both h88 (○) and MBP 87–99. In FIG. 8A, the proliferative response of lymph node cells of SJL mice immunized with MBP 87–99 to A97 (■) was substantially higher than what is seen with native peptide (O). Moreover, lymph node cells from mice immunized with A97 also responded to native peptide (FIG. 8B).

EXAMPLE 5

ANTIGEN-SPECIFIC T CELL LINE PROLIFERATION ASSAYS

Assays for the antigen-specific proliferation assay of T cell lines are performed in 96-well flat bottom microtiter plates (Costar; Cambridge, Mass.), essentially as described previously (Offner et al., 1992; Gold et al., 1992). T cell lines are established as described in Example 3. An initial 1:10 dilution of a 1.5 mM stock solution of MBP or the peptide analogues is added into tissue culture medium. The samples are diluted by three-fold serial dilutions (final volume 100 $\mu$l). The responding continuous T cell lines are resuspended to $4 \times 10^5$ cells per ml and 50 $\mu$l aliquots added to each well ($5 \times 10^4$ cells per well). Splenocyte feeders are also added by first sacrificing Lewis rats, removing their spleens, and making a single cell suspension in tissue culture medium. The splenocytes are then counted, resuspended to $100 \times 10^6$ cells per ml and irradiated at 3000 rad. The cells are then diluted to $20 \times 10^6$ cells per ml and 50 $\mu$l aliquots dispensed into each well ($1 \times 10^6$ cells per well).

Cultures are incubated at 37° C. in humidified air containing 7.5% $CO_2$ for 3 days. Twelve to sixteen hours prior to harvesting, 0.5–1.0 $\mu$Ci of [$^3$H]-thymidine (20 Ci/mM; New England Nuclear) is added to each well and the cultures reincubated. Plates are then harvested with a Matrix filtermate harvester (Packard) and counted using an Automatic Direct Beta Counter (Packard). Mean cpm and the standard error of the mean are calculated from triplicate wells. Results are shown in FIGS. 5A, 5B, 5C and 5D for D-amino acid substitutions at positions 87, 88, 98 and 99, respectively.

Murine MBP-specific T cell clones were also used as targets in proliferation assays. T cell clones (30,000 cells)

were cultured for 72 hr in the presence of MBP 87–99, A97, or PLP 139–151 (myelin proteolipid protein), and irradiated, syngeneic spleen cells. For 18 hr prior to harvesting, [$^3$H]-thymidine was added to each culture. Incorporated thymidine was determined. Data from one clone (AG.1H8) is presented below.

| Peptide | Proliferation (CPM × 10$^{-3}$) | |
| --- | --- | --- |
| | 10 μM | 50 μM |
| MBP (87–99) | 3.2 ± 0.6 | 45.3 ± 5.2 |
| A97 | 48.9 ± 4.7 | 126.8 ± 4.4 |
| PLP 139–151 | 0.15 ± 0.03 | 0.26 ± 0.12 |

Figure 9A:
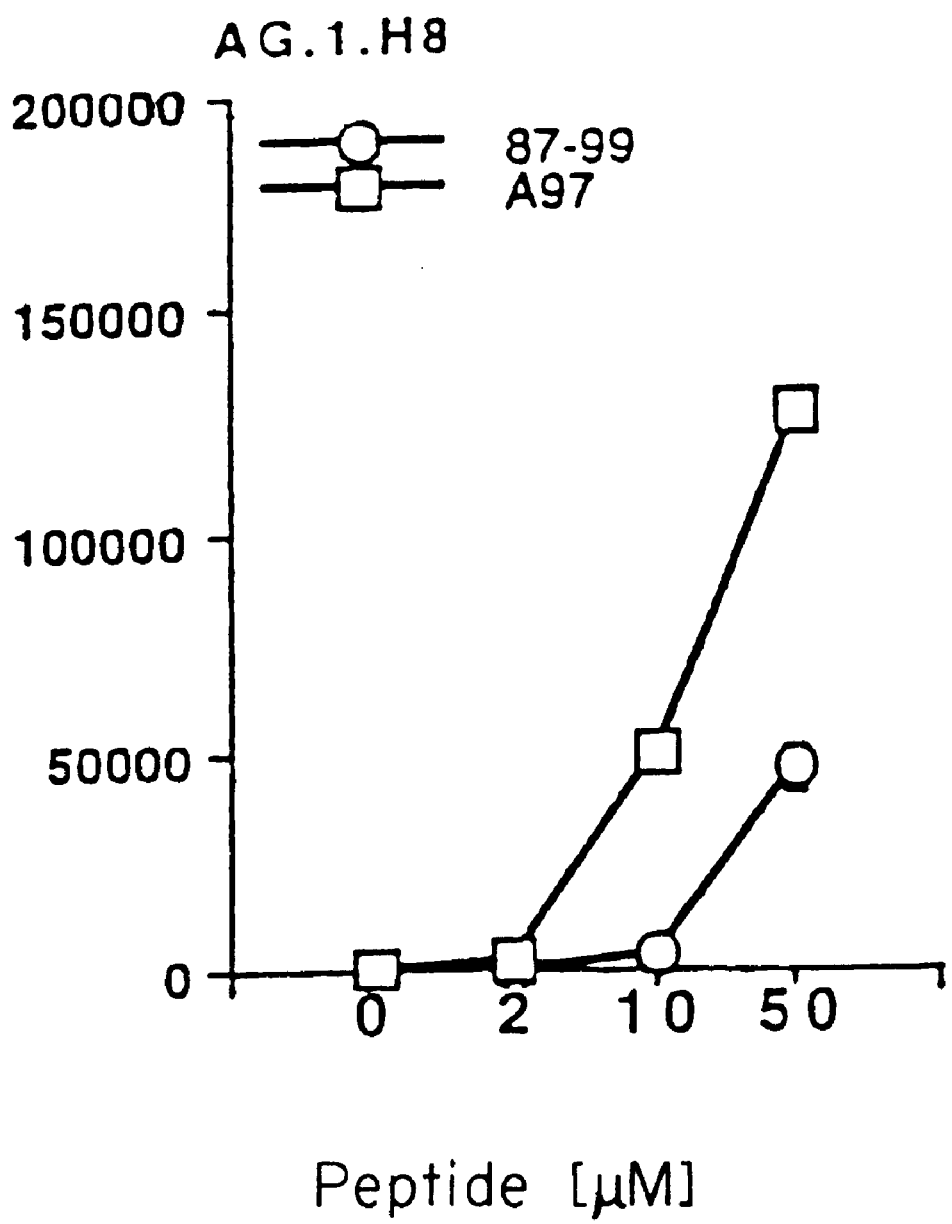
Figure 9B:
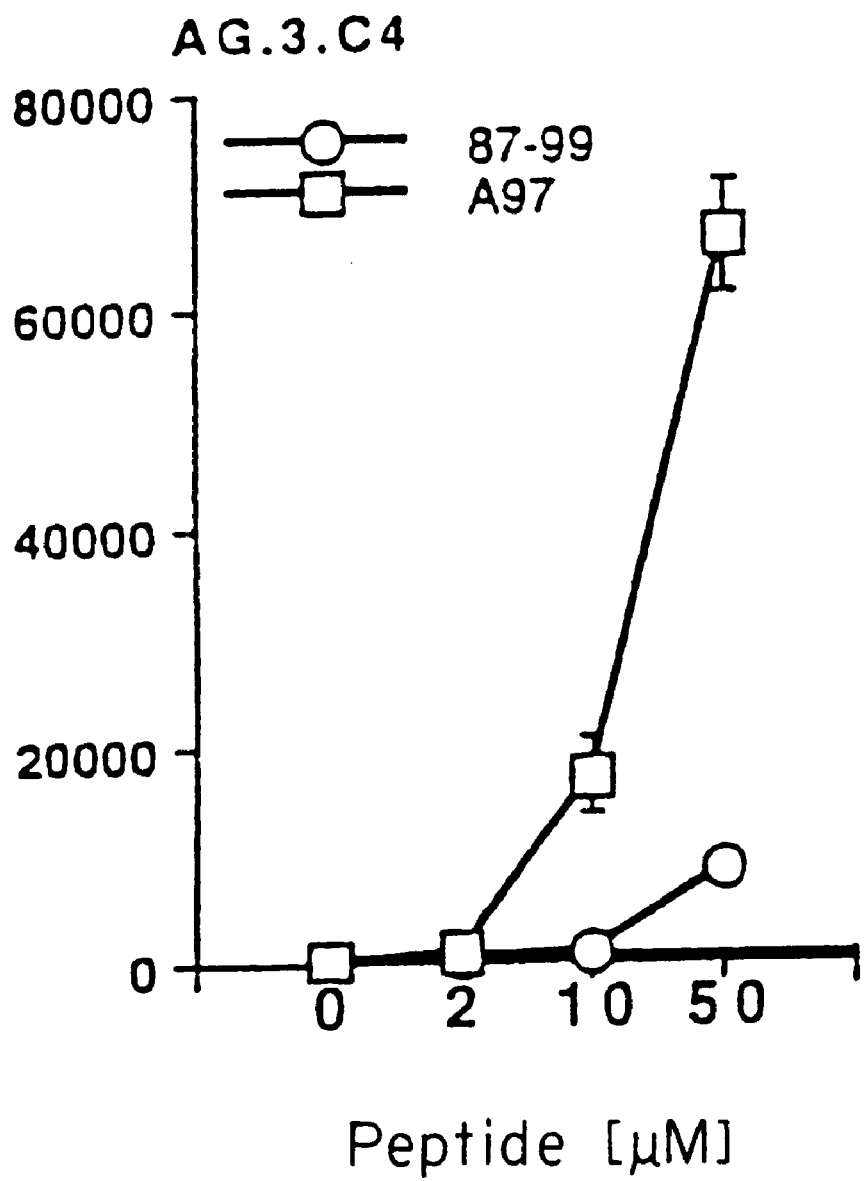
Figure 9C:
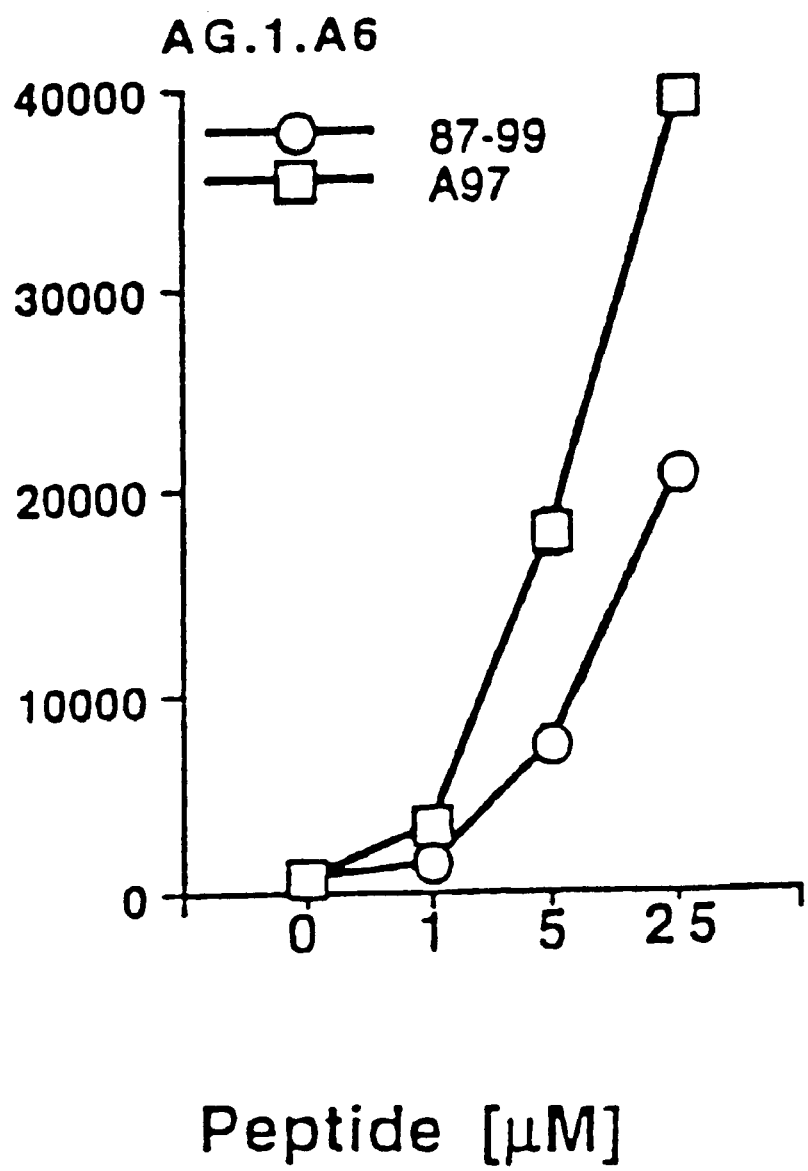

In FIG. 9, proliferative responses of three T cell lines to A97 are also shown to be substantially higher than to native peptide.

A similar pattern of proliferation to A97 was seen with lymph node cells obtained from MBP 87–99 immunized mice. At 10 μM of peptide, A97 induced more proliferation (132,282±10,775 CPM±SEM) than that induced by native peptide (102,585±9,127 CPM). Background counts were 11,431±3,025 CPM.

EXAMPLE 6

IMMUNIZATIONS AND EAE INDUCTION

MBP peptide and peptide analogues are dissolved in phosphate-buffered saline (PBS) and emulsified with an equal volume of incomplete Freund's adjuvant supplemented with 4 mg/ml heat-killed *Mycobacterium tuberculosis* H37Ra in oil (Difco Laboratories, Inc., Detroit, Mich.). Rats are immunized subcutaneously at the base of the tail with 0.2 ml containing 500 μg of peptide in the emulsion and are monitored for clinical signs daily. EAE is scored on a scale of 0–4, as follows: 0, clinically normal; 1, flaccid tail; 2, hind limb weakness; 3, hind limb paralysis; 4, front and hind limbs affected.

EXAMPLE 7

INHIBITION OF MBP 87–99 INDUCED EAE IN LEWIS RATS AND SJL MICE

Female Lewis rats, 6–8 weeks old, are injected with 500 μg of MBP (87–99) in CFA containing 500 μg of *Mycobacterium tuberculosis* H37Ra at the base of the tail in 200 μl. Rats are divided into groups of 5. The control group receives 0.5 ml of SWM 110–121 and the treatment group receives the peptide analogue (1 mg/0.5 ml PBS) intraperitoneally, on days 9 and 10 (or 10 and 11) after immunization. Animals are monitored on a daily basis for disease symptoms. EAE is recorded on the following scale: 0, no symptoms; 1, tail paralysis; 2, hind limb weakness; 3, hind limb paralysis; 4, hind and front limbs affected.

Figure 6A:
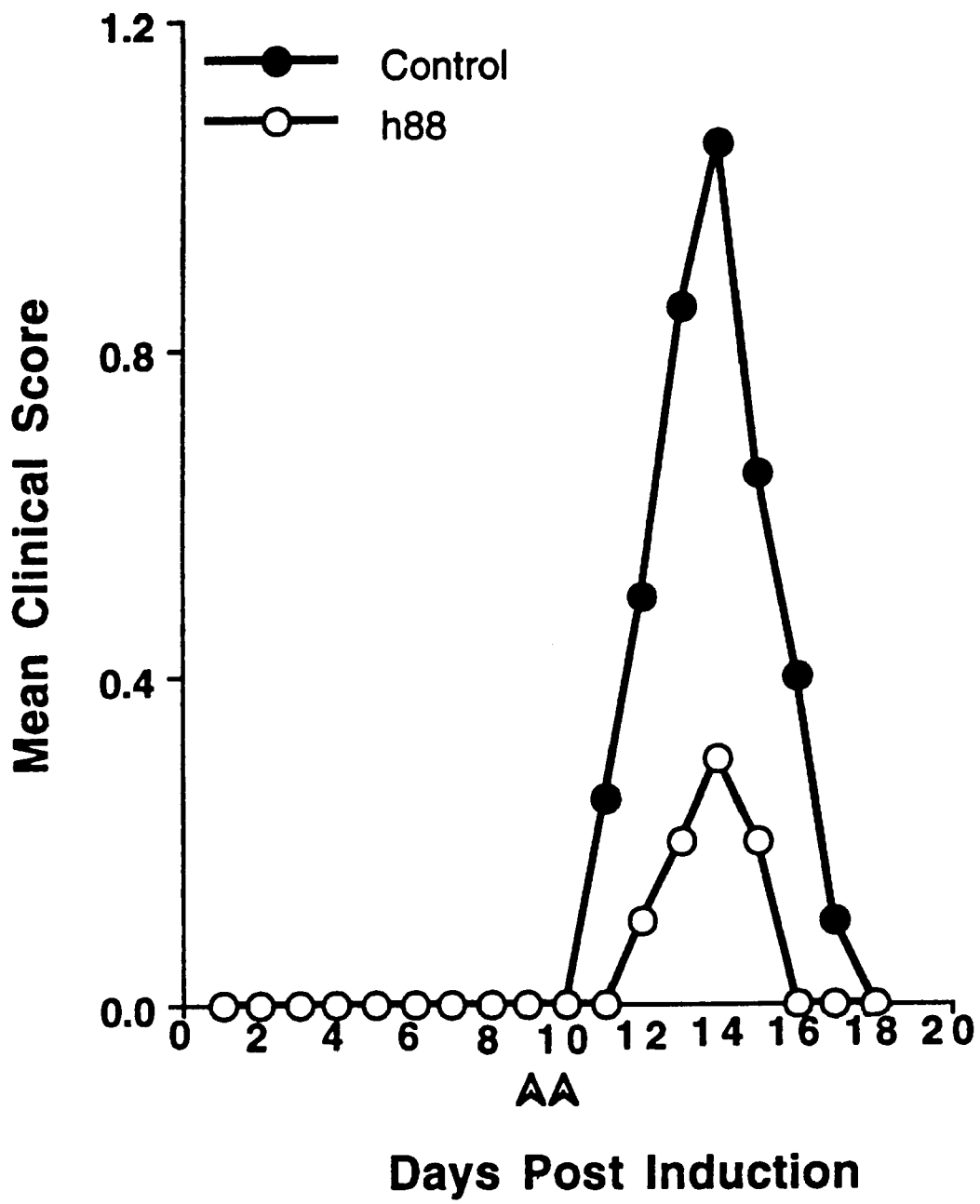
Figure 6B:
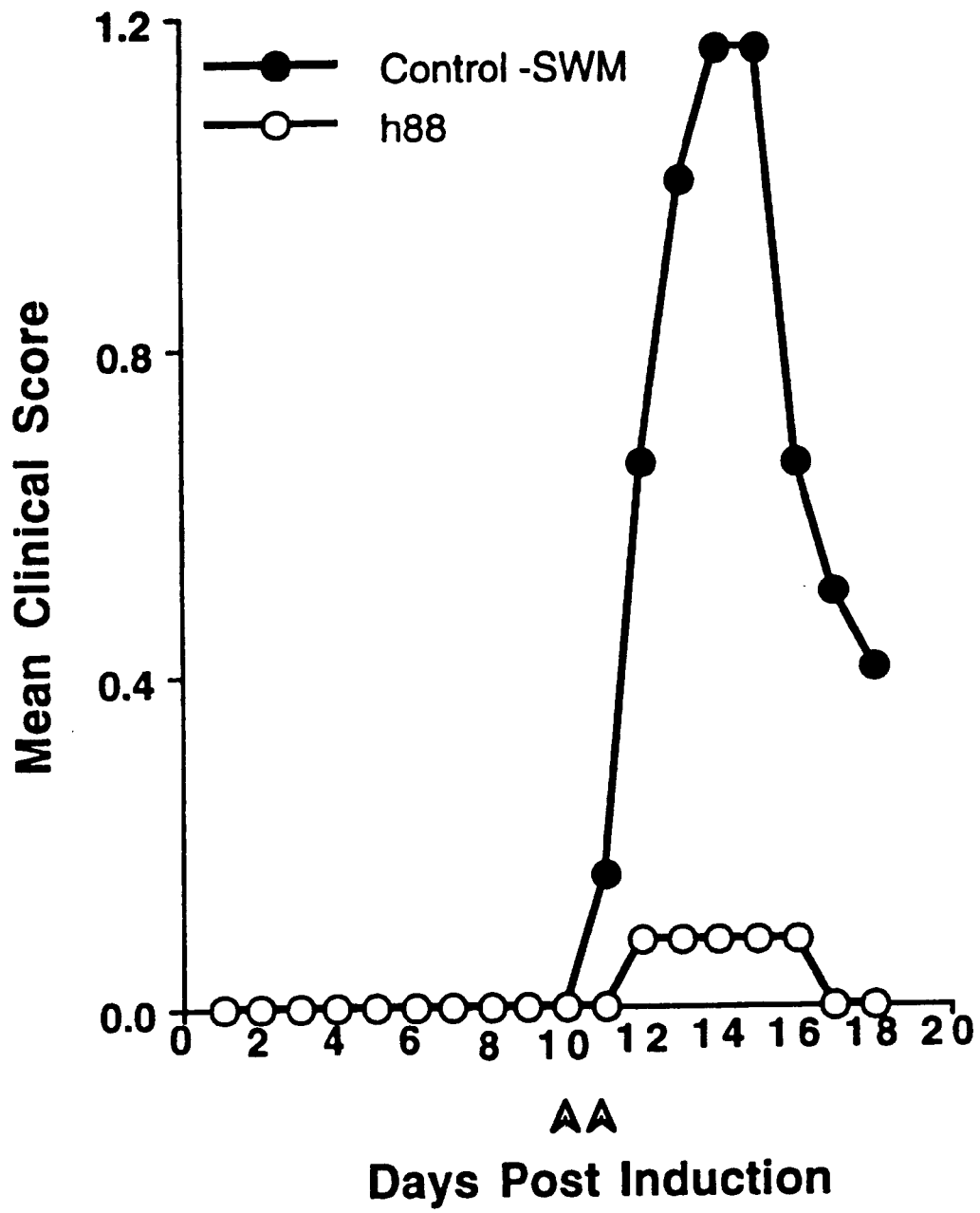
Figure 6C:
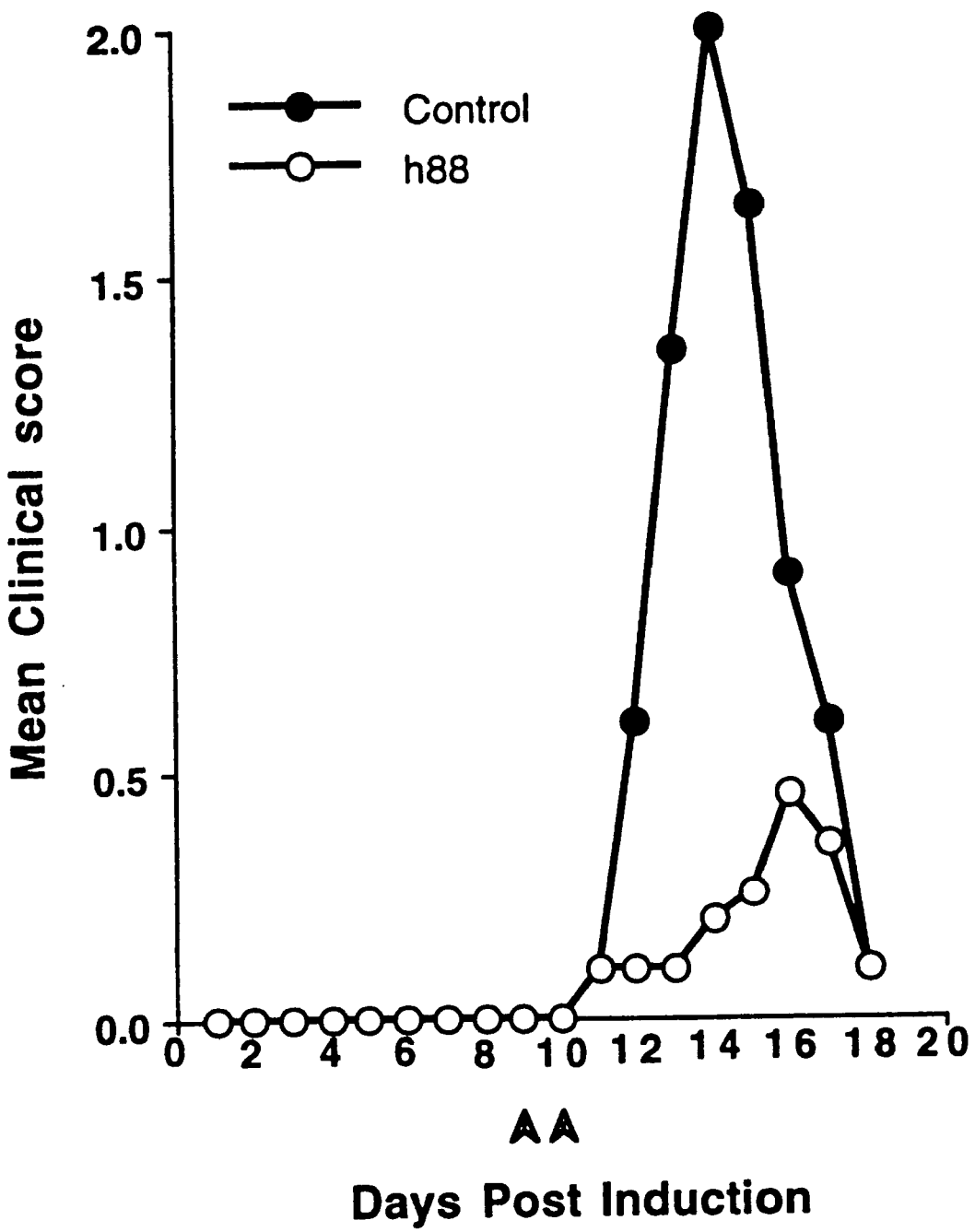

Results of three separate experiments are provided in FIGS. 6A, 6B and 6C. Briefly, as is evident from these graphs, h88 lessens the mean clinical score of MBP-induced EAE.

Inhibition of induction of EAE may also be measured in mice. EAE is induced in a group of 10 SJL mice by subcutaneous immunization with 250 μg of MBP 87–99 in CFA-containing 500 μg heat killed H37Ra strain of *Mycobacterium tuberculosis*. At weekly intervals for five weeks following the initial injection, mice are injected intraperitoneally with 0.1 ml of 4 mg/ml aqueous solution of either A97 (□) or control peptide (O). Mice are monitored daily for disease symptoms and are scored for disease severity on the following scale: 0, no signs; 0.5, Weak tail; 1, Limp tail; 2, Weak hind limbs with ataxia; 3, Hind limb paralysis; 4, Moribund; 5, Death. The score is expressed as the mean clinical score on each day for all mice in the group. If a mouse dies of EAE, a score of 5 is included for that animal in calculations for all subsequent days of analysis.

Figure 10:
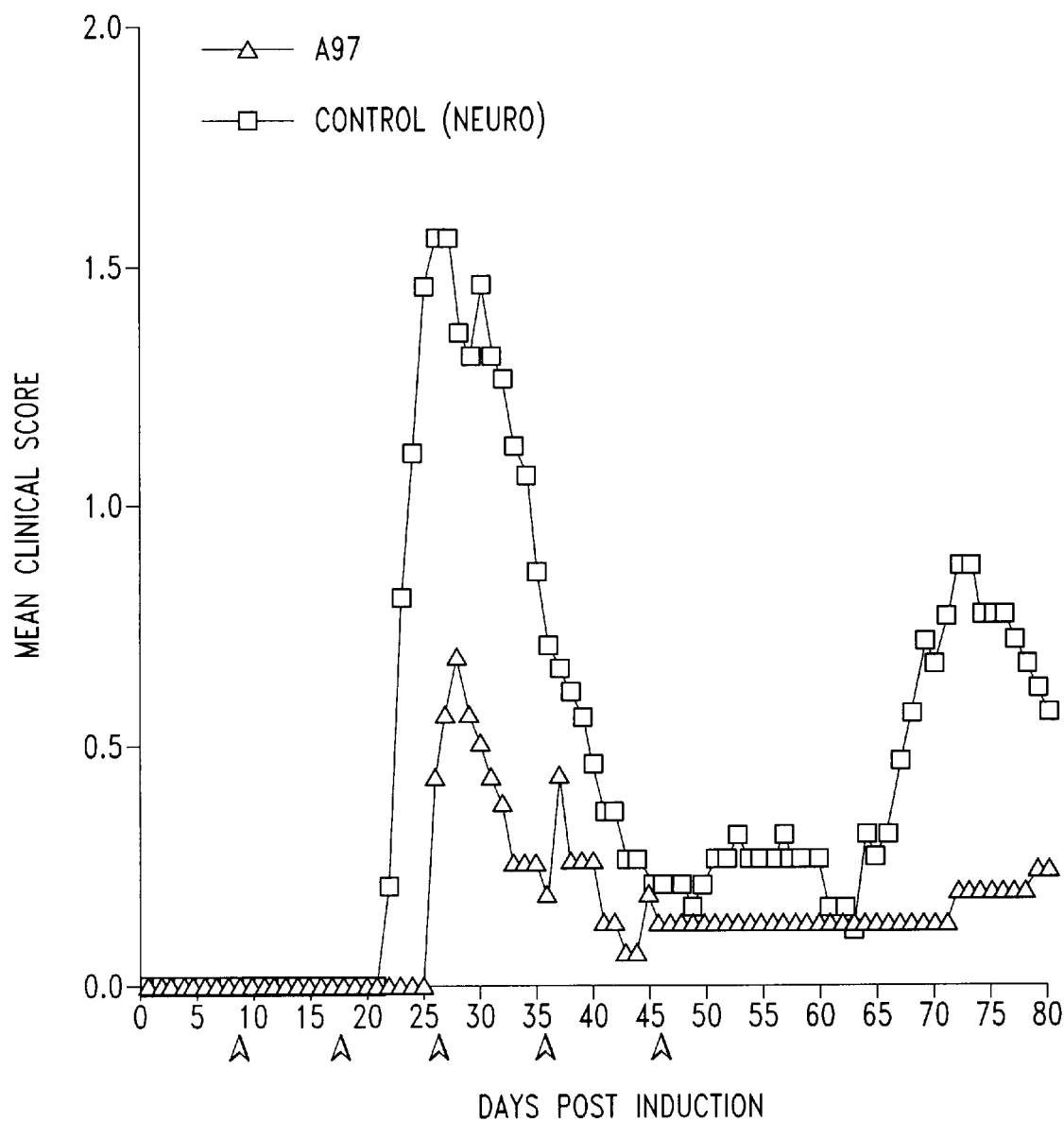

As shown in FIG. 10, treatment of SJL mice with soluble A97 injected i.p. following EAE induction with MBP (87–99) decreased the mean clinical score of EAE. In addition, the incidence of disease was reduced from 90% in the control group to 50% in the A97-treated group. Moreover, while about 70% of the mice treated with native peptide only exhibited a relapse, almost no mice treated with A97 experienced a relapse (FIG. 10).

EXAMPLE 8

INDUCTION OF EAE BY PEPTIDE ANALOGUE

The ability of peptide analogues to cause EAE is assessed in vivo. Briefly, 6–8 week old Lewis rats are injected sub-cutaneously with MBP 87–99 (○), or analogue (□).

A 200 μl innoculum containing 500 μg of peptide emulsified with CFA containing 5 mg/ml H37Ra is used for each rat. Rats start showing symptoms of EAE around day 10 following immunization and are monitored daily for disease severity on the following scale: 0—no symptoms, 0.5—tail affected, 1—tail paralyzed (limp), 2—hind limbs affected, 3—hind limbs paralyzed, 4—fore limbs also affected. Data is represented as mean of clinical score of each of the 6 animals in each group on a given day.

Figure 7:
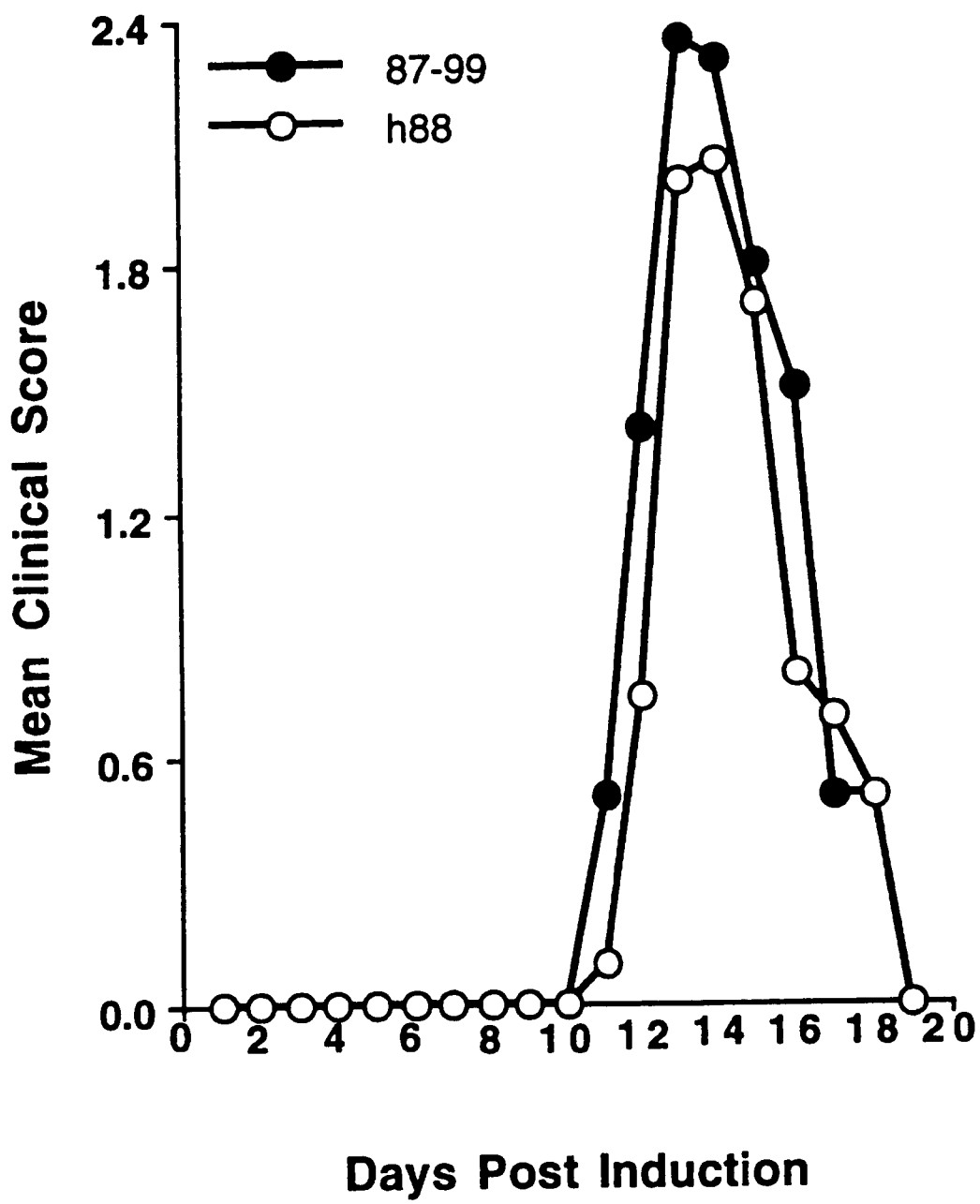
Figure 8A:
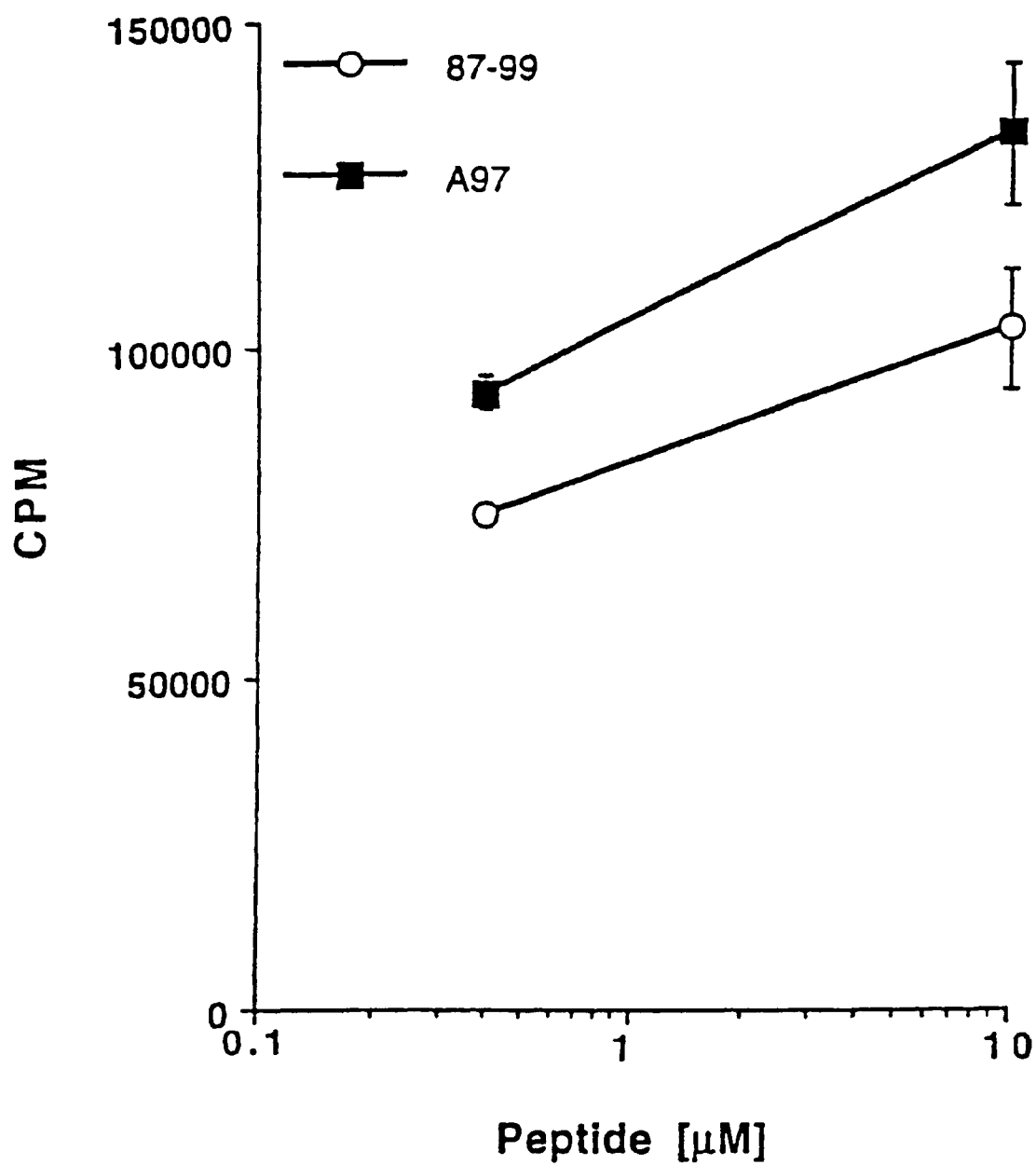
Figure 8B:
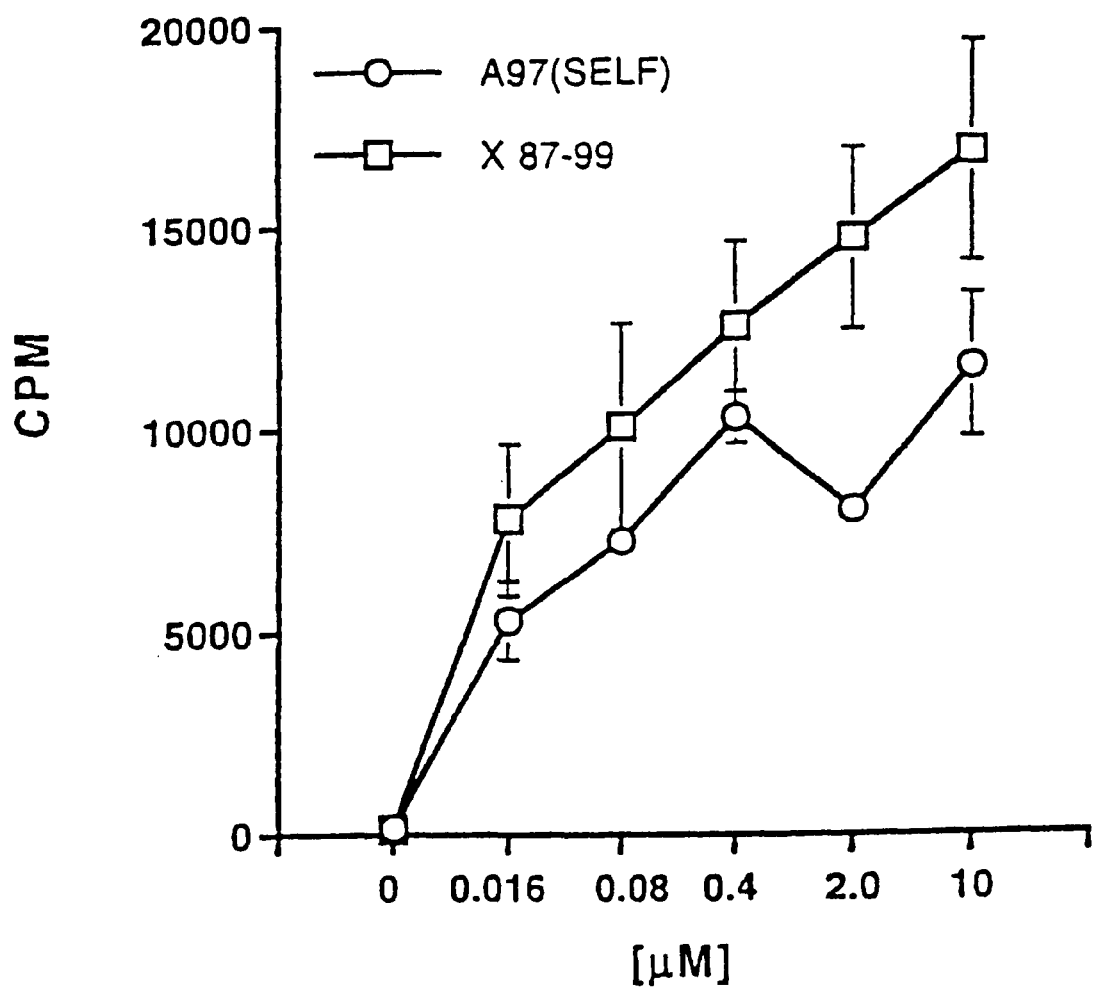

As can be seen in FIG. 7, both MBP 87–99 and h88 (when injected with CFA) induced EAE in rats, whereas h88 alone (without CFA) does not induce EAE in rats (data not shown).

Figure 11:
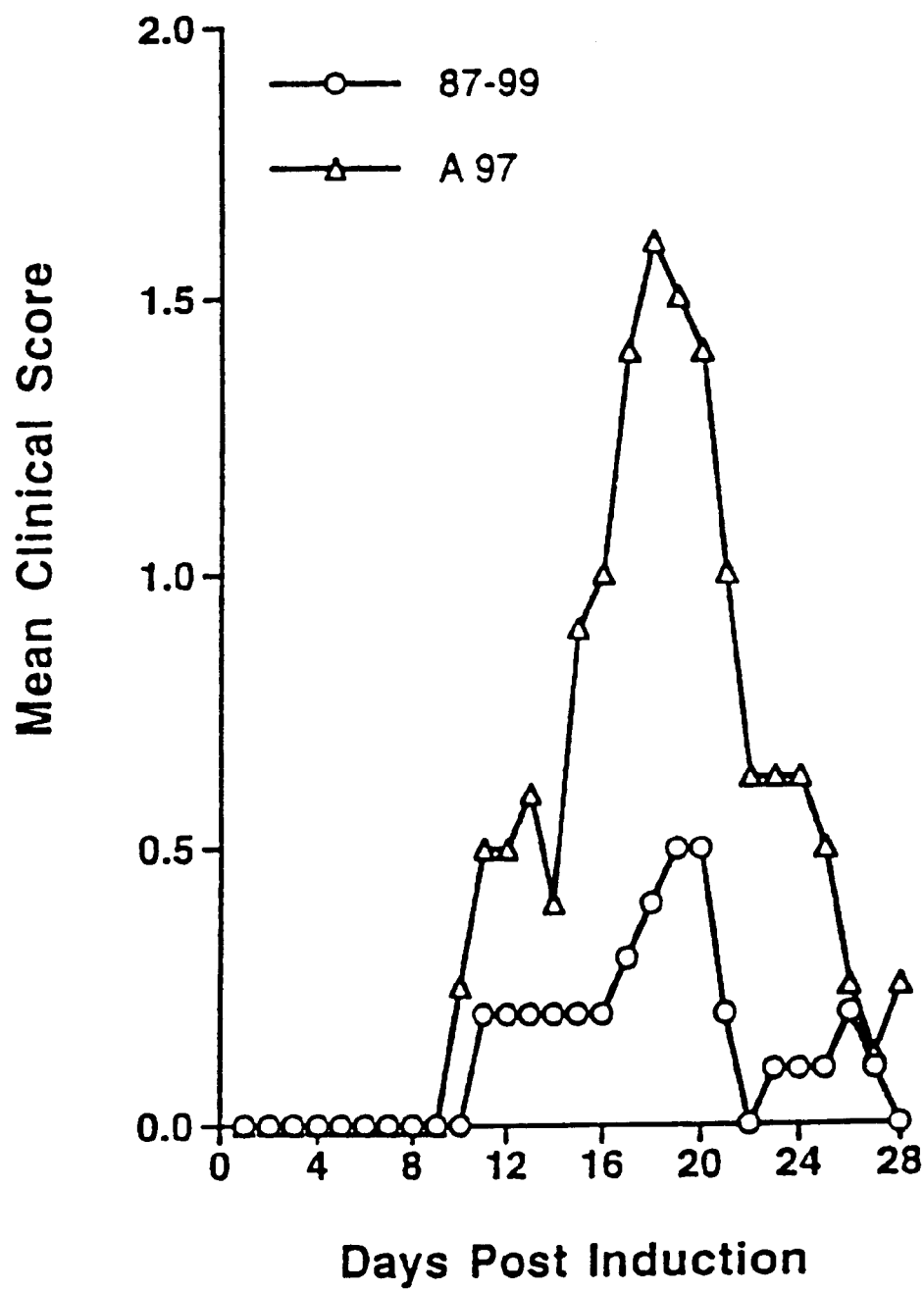

Similarly, mice are injected with a single, 250 μg dose of MBP (87–99) or A97 in CFA containing 500 μg of heat killed Mycobacterium. Pertussis toxin (400 ng/mouse) is injected i.v. at day 0 and day 2. Mice are assessed for disease symptoms as described above. As shown in FIG. 11, mice had an increased mean clinical score following injection of A97, with all animals (5/5) developing disease.

EXAMPLE 9

INDUCTION OF APOPTOSIS

An IL-2 stimulated T cell line that is reactive to MBP 87–99 is restimulated with native MBP peptide or analogue, and the induction of apoptosis is measured. The T cell line is restimulated for 48 hr with 10-fold excess of irradiated (3000 rads) SJL T cell depleted splenocytes, 50 IU/ml hIL-2, and either 1 μM, 3 μM, or 10 μM of MBP 87–99, 97A, neurotensin or PLP. In a separate assay, cells are restimulated with 10 μg/ml anti-CD3 monoclonal antibody instead of peptide. Cell loss is measured by flow cytometry as described in *Current Protocols in Immunology* (Section 3.17, John Wiley and Sons, N.Y., 1992).

Figure 12:
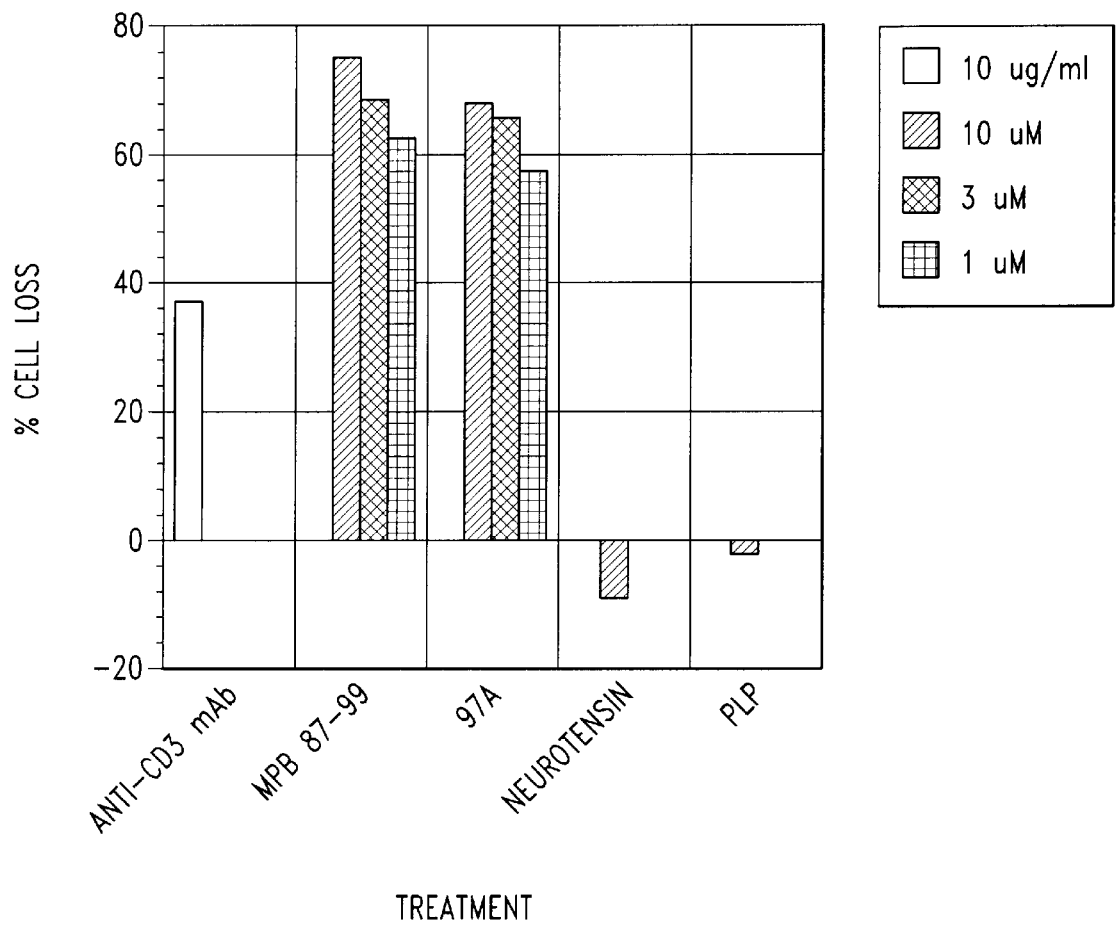

As shown in FIG. 12, A97 caused activation-induced apoptosis to the same extent as native peptide at concentrations as low as 1 μM.

EXAMPLE 10

CYTOKINE PRODUCTION INDUCED BY PEPTIDE ANALOGUES

Cytokine production by an IL-2 stimulated T cell line, which is reactive to MBP 87–99, is measured in response to various peptides and peptide analogues. The activated T cell line is co-cultured for 48 hr with a 10-fold excess of irradiated (3000 Rads) SJL T cell-depleted spleen cells, 50 IU/ml human rIL-2 and 10 $\mu$M PLP 139–151, 3 $\mu$M A97, or 3 $\mu$M MBP 87–99. Cytokine release is measured by ELISA.

As shown in the Table below, A97 induced the production of IL-2, IL-4 and $\gamma$-IFN to the same extent as native peptide. Moreover, the ratio of $\gamma$-IFN/IL-4 favored cytokines secreted by Th1 cells. No IL-10 or TNF-$\alpha$ was detected.

|       | PLP   | A97   | MBP 87–99 |
|-------|-------|-------|-----------|
| IL-2  | 1646* | 12741 | 11708     |
| IL-4  | 2197  | 11716 | 19760     |
| $\gamma$-IFN | 3073  | 54447 | 55841     |

*pg/ml

EXAMPLE 11

ACTIVATION OF T CELLS

Activation of T cells is measured by the extent of phosphorylation of the CD3 zeta chain. Tyrosine phosphorylation of zeta chain is one of the earliest steps in a cascade of events leading to T cell activation. MBP 87–99 specific T cells ($1.4 \times 10^7$) are added to T cell-depleted SJL splenocytes ($2.8 \times 10^7$), which are pre-incubated with PLP 139–151, MBP 87–99, or A97 (20 $\mu$M) for 1 hr at 37° C. The cells are briefly centrifuged and incubated for 3 min at 37° C. Cells are then washed once in ice-cold PBS containing 0.5 mM EDTA and 0.5 mM sodium orthovanadate. Cells are lysed in 1 ml of 20 mM Tris, pH 7.5, 150 mM NaCl, 1% NP-40, 10 mM EDTA, 1 mM sodium orthovanadate, 1 mM PMSF, 10 $\mu$g/ml aprotinin, and 10 $\mu$g/ml leupeptin for 45 min on ice. Following centrifugation, zeta chain is immunoprecipitated from supernates using agarose conjugated-anti-zeta chain antibody (clone 6B10.2). Immunoprecipitates are washed three times in lysis buffer, once in PBS and subsequently resuspended in 2x Laemmli sample buffer. The immunoprecipitated material is electrophoresed in a 10% SDS-PAGE gel and transferred to nitrocellulose membrane. The membrane is blocked with 2% BSA, 0.5% ovalbumin, 2.5% non-fat dry milk, 10 mM Tris (pH 7.4), and 150 mM NaCl for 1 hr at room temperature. Phosphotyrosine is detected using 1 $\mu$g/ml 4G10 antibody followed by peroxidase conjugated-goat anti-mouse IgG. Blots are developed using a chemiluminescence substrate.

Figure 13:
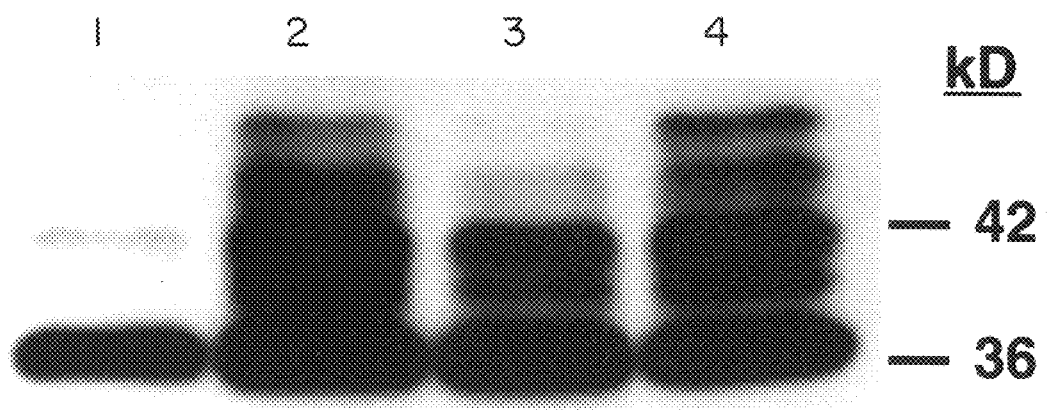

As shown in FIG. 13, TCR zeta chain had approximately equivalent phosphorylation following treatment of T cells with A97 and MBP 87–99.

From the foregoing, it will be evident that although specific embodiments of the invention have been described herein for the purpose of illustrating the invention, various modifications may be made without deviating from the spirit and scope of the invention.

---

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 516 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..513

(xi) SEQUENCE DESCRIPTION: SEQ ID NO:1:

```
ATG GCG TCA CAG AAG AGA CCC TCC CAG AGG CAC GGA TCC AAG TAC CTG         48
Met Ala Ser Gln Lys Arg Pro Ser Gln Arg His Gly Ser Lys Tyr Leu
 -1   1               5                  10                  15

GCC ACA GCA AGT ACC ATG GAC CAT GCC AGG CAT GGC TTC CTC CCA AGG         96
Ala Thr Ala Ser Thr Met Asp His Ala Arg His Gly Phe Leu Pro Arg
                 20                  25                  30

CAC AGA GAC ACG GGC ATC CTT GAC TCC ATC GGG CGC TTC TTT GGC GGT        144
His Arg Asp Thr Gly Ile Leu Asp Ser Ile Gly Arg Phe Phe Gly Gly
                 35                  40                  45

GAC AGG GGT GCG CCA AAG CGG GGC TCT GGC AAG GAC TCA CAC CAC CCG        192
Asp Arg Gly Ala Pro Lys Arg Gly Ser Gly Lys Asp Ser His His Pro
```

-continued

```
                  50                  55                  60
GCA AGA ACT GCT CAC TAT GGC TCC CTG CCC CAG AAG TCA CAC GGC CGG        240
Ala Arg Thr Ala His Tyr Gly Ser Leu Pro Gln Lys Ser His Gly Arg
         65                  70                  75

ACC CAA GAT GAA AAC CCC GTA GTC CAC TTC TTC AAG AAC ATT GTG ACG        288
Thr Gln Asp Glu Asn Pro Val Val His Phe Phe Lys Asn Ile Val Thr
 80                  85                  90                  95

CCT CGC ACA CCA CCC CCG TCG CAG GGA AAG GGG AGA GGA CTG TCC CTG        336
Pro Arg Thr Pro Pro Pro Ser Gln Gly Lys Gly Arg Gly Leu Ser Leu
                100                 105                 110

AGC AGA TTT AGC TGG GGG GCC GAA GGC CAG AGA CCA GGA TTT GGC TAC        384
Ser Arg Phe Ser Trp Gly Ala Glu Gly Gln Arg Pro Gly Phe Gly Tyr
                115                 120                 125

GGA GGC AGA GCG TCC GAC TAT AAA TCG GCT CAC AAG GGA TTC AAG GGA        432
Gly Gly Arg Ala Ser Asp Tyr Lys Ser Ala His Lys Gly Phe Lys Gly
                130                 135                 140

GTC GAT GCC CAG GGC ACG CTT TCC AAA ATT TTT AAG CTG GGA GGA AGA        480
Val Asp Ala Gln Gly Thr Leu Ser Lys Ile Phe Lys Leu Gly Gly Arg
                145                 150                 155

GAT AGT CGC TCT GGA TCA CCC ATG GCT AGA CGC TGA                        516
Asp Ser Arg Ser Gly Ser Pro Met Ala Arg Arg
160                 165                 170
```

(2) INFORMATION FOR SEQ ID NO:2:

(i) SEQUENCE CHARACTERISTICS:
        (A) LENGTH: 171 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Ser Gln Lys Arg Pro Ser Gln Arg His Gly Ser Lys Tyr Leu
 -1  1               5                  10                  15

Ala Thr Ala Ser Thr Met Asp His Ala Arg His Gly Phe Leu Pro Arg
                 20                  25                  30

His Arg Asp Thr Gly Ile Leu Asp Ser Ile Gly Arg Phe Phe Gly Gly
                 35                  40                  45

Asp Arg Gly Ala Pro Lys Arg Gly Ser Gly Lys Asp Ser His His Pro
                 50                  55                  60

Ala Arg Thr Ala His Tyr Gly Ser Leu Pro Gln Lys Ser His Gly Arg
         65                  70                  75

Thr Gln Asp Glu Asn Pro Val Val His Phe Phe Lys Asn Ile Val Thr
 80                  85                  90                  95

Pro Arg Thr Pro Pro Ser Gln Gly Lys Gly Arg Gly Leu Ser Leu
                100                 105                 110

Ser Arg Phe Ser Trp Gly Ala Glu Gly Gln Arg Pro Gly Phe Gly Tyr
                115                 120                 125

Gly Gly Arg Ala Ser Asp Tyr Lys Ser Ala His Lys Gly Phe Lys Gly
                130                 135                 140

Val Asp Ala Gln Gly Thr Leu Ser Lys Ile Phe Lys Leu Gly Gly Arg
                145                 150                 155

Asp Ser Arg Ser Gly Ser Pro Met Ala Arg Arg
160                 165                 170
```

What is claimed is:

1. A peptide analogue comprising at least seven consecutive amino acids selected from residues 86 to 99 of human myelin basic protein, including residue 97, wherein the L-arginine at position 97 is altered to a D-amino acid, said peptide analogue having increased MHC binding relative to MBP 87–99.

2. The peptide analogue of claim 1 wherein the L-arginine at position 97 is altered to D-alanine.

3. The peptide analogue of claim 1 wherein the L-arginine at position 97 is altered to a D-amino acid selected from the group consisting of D-arginine, D-asparagine, D-aspartic acid, D-cysteine, D-glutamine, D-glutamic acid, D-glycine, D-histidine, D-isoleucine, D-leucine, D-lysine, D-methionine, D-phenylalanine, D-proline, D-serine, D-threonine, D-tryptophan, D-tyrosine and D-valine.

4. The peptide analogue according to claim 1 wherein the N-terminal and/or C-terminal amino acids are altered to a D-amino acid, such that upon administration of the peptide analogue in vivo proteolysis is reduced.

5. A peptide analogue comprising at least seven consecutive amino acids selected from residues 86 to 99 of human myelin basic protein, including residue 97, wherein the L-arginine at position 97 is altered to L-alanine.

6. A composition comprising a peptide analogue according to any one of claims 1–4 or 5, in combination with a pharmaceutically acceptable carrier or diluent.

* * * * *